United States Patent
Taira et al.

(10) Patent No.: US 6,635,683 B1
(45) Date of Patent: Oct. 21, 2003

(54) FILM RESPONSIVE TO BICARBONATE ION

(75) Inventors: Hiroaki Taira, Tsukuba (JP); Kazuya Ibaragi, Tsukuba (JP); Hiromasa Yamamoto, Tsukuba (JP); Hiroyuki Yanagi, Hiratsuka (JP)

(73) Assignee: Tokuyama Corporation, Yamaguchi (JP)

(*) Notice: Subject to any disclaimer, the term of this patent is extended or adjusted under 35 U.S.C. 154(b) by 0 days.

(21) Appl. No.: 09/744,582

(22) PCT Filed: Jul. 23, 1999

(86) PCT No.: PCT/JP99/03947
§ 371 (c)(1),
(2), (4) Date: Jan. 26, 2001

(87) PCT Pub. No.: WO00/07004
PCT Pub. Date: Feb. 10, 2000

(30) Foreign Application Priority Data

Jul. 28, 1998 (JP) .............................. 10/212579

(51) Int. Cl.⁷ .................................................. C08J 5/22
(52) U.S. Cl. ..................... 521/27; 521/25; 522/31; 522/904; 524/183; 524/236; 524/251; 524/154; 106/287.29; 106/287.3; 106/287.32; 568/6
(58) Field of Search ................ 521/25, 27; 522/31, 522/904; 524/183, 236, 251, 154; 106/287.29, 287.3, 287.32; 568/6

(56) References Cited

U.S. PATENT DOCUMENTS 3,723,281 A   3/1973   Wise

FOREIGN PATENT DOCUMENTS

| EP | 0 155 162 | 9/1985 |
|----|-----------|--------|
| EP | 0 245 168 | 11/1987 |
| JP | 1-501094  | 4/1989 |
| JP | 3-501519  | 4/1991 |
| JP | 4-204368  | 7/1992 |
| JP | 9-54065   | 2/1997 |

OTHER PUBLICATIONS

J. Greenberg et al., Analytica Chimica Acta, 141, pp. 57–64 (1982).

U. Oesch et al., J. Chem. Soc., Faraday Trans. 1, 82, pp. 1179–1186 (1986).

*Primary Examiner*—Nathan M. Nutter
*Assistant Examiner*—Melanie Bissett
(74) *Attorney, Agent, or Firm*—Wenderoth, Lind & Ponack, LLP

(57) ABSTRACT

A membrane sensitive to anions is obtained by forming into a membrane either a composition comprising an onium salt compound such as trioctylmethylammonium chloride or tetraoctylammonium bromide, and an aromatic boric diester compound such as (p-alkyloxy)phenyl borate, or a composition which comprises these two ingredients and a membrane-forming polymer such as polyvinyl chloride or polystyrene, and may further contain a fat-soluble anion salt such as tetraphenyl borate. This membrane can yield an ion-selective electrode which permits hydrogencarbonate ions contained in body fluids to be rapidly determined with high sensitivity and high selectivity and which has a long life.

22 Claims, 2 Drawing Sheets

FILM RESPONSIVE TO BICARBONATE ION

TECHNICAL FIELD

This invention relates to a bicarbonate ion-sensitive membrane which is useful in the construction of an ion-selective electrode for measuring the activity of bicarbonate ion in a solution. More particularly, this invention relates to an anion-sensitive membrane which contains an aromatic boric diester structural unit and an onium salt structural unit and which, when it is used as the boundary membrane of an ion-selective electrode, can detect bicarbonate ions (i.e., hydrogencarbonate ions) selectively.

BACKGROUND ART

In recent years, attempts are being extensively made to apply ion-selective electrodes to medical fields and thereby determine various ions contained in biological fluids such as blood and urine. Its purpose is to measure the concentrations of specific ions in biological fluids and thereby diagnose various diseases, on the basis of the fact that such ion concentrations are closely related with metabolic reactions in the living body. At present, ion-selective electrodes are being used to measure the concentrations of sodium ion, potassium ion and chloride ion in biological fluids, so that these ion concentrations can be measured conveniently and rapidly.

Generally, as illustrated in FIG. 1, an ion-selective electrode is basically constructed by providing a cylindrical vessel 11 with a barrier membrane comprising an anion-sensitive membrane 12 at the part thereof which is to be immersed in sample solutions (generally at the bottom thereof) and placing therein an internal electrolyte 13 and an internal reference electrode 14.

FIG. 2 illustrates a typical construction of an ion measuring apparatus for measuring the activity of an ion in a solution by using such an ion-selective electrode. Specifically, an ion-selective electrode 21, together with a salt bridge 22, is immersed in a sample solution 23. The other end of the salt bridge, together with an external reference 24, is immersed in a saturated potassium chloride solution 26. The potential difference between both electrodes is read with an electrometer 25, and the ionic activity of a specific ionic species in the sample solution can be determined from the potential difference. The performance of the ion-selective electrode used in such an ion measuring apparatus is greatly affected by the performance of the ion-sensitive membrane used therein.

Hydrogencarbonate ion is one of the important ions present in biological fluids, particularly blood. Since hydrogencarbonate ion is an important factor in revealing the state of respiratory and metabolic functions in the living body, information useful for the diagnosis of various diseases such as diabetes mellitus and renal disorders can be obtained by the measurement of Hydrogencarbonate ion. At present, hydrogencarbonate ion concentrations are calculated from the pH of the sample and the measured value of carbon dioxide partial pressure ($P_{CO2}$) according to the following equation.

$$pH=6.1+\log\{[HCO_3^-]/0.03 \cdot PCO_2\}$$

This method requires a measuring time of as long as about 30 to 60 seconds. Moreover, it is necessary to employ a measuring method different from that for the aforesaid sodium ion-, potassium ion- and chloride ion-selective electrodes. Consequently, it is necessary to measure hydrogencarbonate ion concentrations in a system different from that for the measurement of sodium and potassium ion concentrations.

Generally, ion-selective electrodes can reduce the time required for measurement to the order of several seconds. Moreover, the concentrations of various ions can be simultaneously measured by using a combination of ion-selective electrodes corresponding to ionic species to be measured. Owing to these advantages, a variety of anion-sensitive membranes for the selective detection of hydrogencarbonate ion have conventionally been proposed. They include, for example, (a) a membrane obtained by mixing a polymer (e.g., polyvinyl chloride) with a fat-soluble cation salt (e.g., a quaternary ammonium salt), a trifluoroacetophenone derivative (e.g., trifluoro-acetyl-p-alkylbenzene) and a plasticizer, and forming this mixture into a membrane; and (b) a membrane obtained by mixing a polymer (e.g., polyvinyl chloride) with an organotin compound (e.g., trioctyltin chloride) and a plasticizer and optionally with a trifluoroacetophenone derivative (e.g., trifluoroacetyl-p-alkylbenzene), and forming this mixture into a membrane.

Ion-selective electrodes using the anion-sensitive membrane of the aforesaid type (a) include, for example, an electrode disclosed by Wise et al. (U.S. Pat. No. 3,723,281), an electrode reported by Greenberg et al. [J. Greenberg et al., Anal. Chim. Acta, 141: p. 57–64 (1982)], an electrode disclosed by Chapoteau et al. (Japanese Laid-Open Patent No. 10759/'86=EP-A-155162), and an electrode disclosed by Yamaguchi et al. (Japanese Laid-Open Patent No. 265559/'87=EP-A-245168).

Moreover, ion-selective electrodes using the anion-sensitive membrane of the aforesaid type (b) include an electrode reported by Oesch et al. [J. Oesch et al., J. Chem. Soc. Faraday Trans. 1, 82: p. 1179–1186 (1986)], an electrode disclosed by Ushizawa et al. (Japanese Laid-Open Patent No. 204368/'92), and the like.

However, the ion-selective electrodes using the anion-sensitive membrane of the aforesaid type (a) are known to have poor selectivity relative to fat-soluble ions such as nitrate and thiocyanate ions. Moreover, they also have the disadvantage that their electric potential response is relatively slow (about 1 minute) and their lives are short because the ion-sensitive substance present in the membrane gradually dissolves in the solution.

On the other hand, the ion-selective electrodes using the anion-sensitive membrane of the aforesaid type (b) are known to have poor selectivity relative to chloride ion, because an organotin compound is contained in the membrane. Moreover, they also have the disadvantage that their lives are short because the ion-sensitive substance present in the membrane gradually dissolves in the solution.

Accordingly, it is desired to develop an anion-sensitive membrane capable of yielding an ion-selective electrode which permits hydrogencarbonate ions contained in biological fluids to be rapidly determined with high selectivity and which has a long life.

The present inventors have carried out intensive investigations with a view to developing an anion-sensitive membrane which can solve the above-described problems. As a result, it has now been found that, when a polymer membrane formed by using an onium salt compound and an organic boric diester compound is used as an anion-sensitive membrane, hydrogencarbonate ions present in a solution can be rapidly determined with high selectivity and, moreover, the membrane has a long life. The present invention has been completed on the basis of this finding.

DISCLOSURE OF THE INVENTION

According to the present invention, there is provided a membrane sensitive to bicarbonate ion comprising a polymer membrane which contains an onium salt structural unit (A) and an aromatic boric diester structural unit (B) of the formula

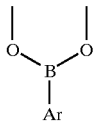

wherein Ar is an aromatic carbocyclic group which may optionally have one or more substituents, either in the form of low-molecular-weight compounds dispersed in the polymer or in a form introduced into a polymer molecule.

Figure 1:
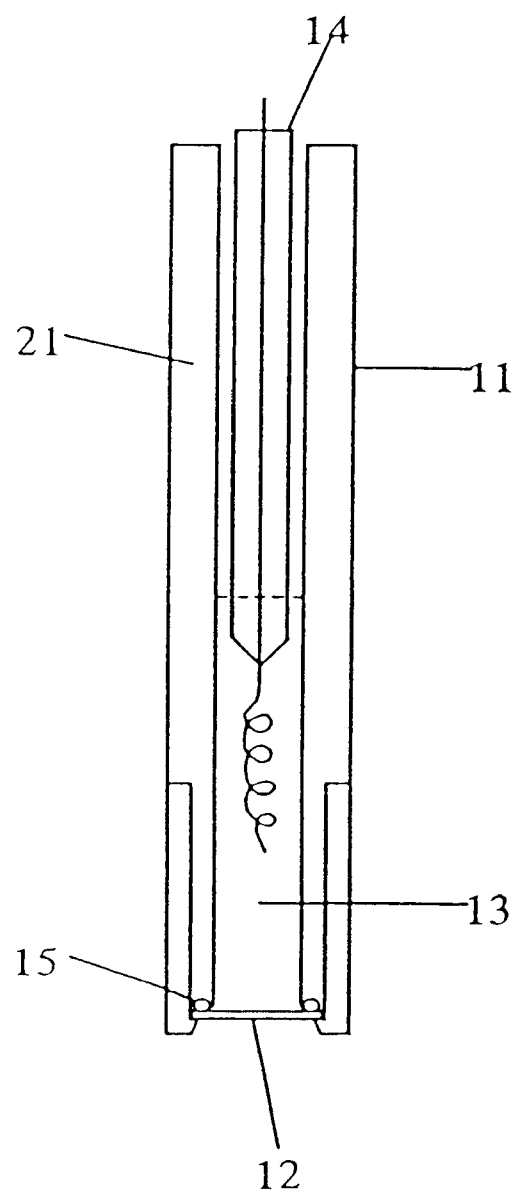
FIG. 1 is a cross-sectional view of an ion-selective electrode using an anion-sensitive membrane.

The bicarbonate ion-sensitive membrane of the present invention will be more specifically described hereinbelow.

EMBODIMENTS OF THE INVENTION

A polymer membrane in accordance with the present invention contains:.

(1) an onium salt structural unit (A), and (2) an aromatic boric diester structural unit (B) of the formula

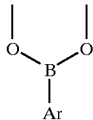

wherein Ar is an aromatic carbocyclic group which may optionally have one or more substituents. In the polymer membrane, these structural units (A) and (B) may be present in any suitable form. For example, each of the structural units (A) and (B) may take the form of a low-molecular-weight compounds dispersed in a polymer matrix, or at least one of the structural units (A) and (B) may be present in a form introduced into a polymer molecule. Where any one of the structural units (A) and (B) is present in a form introduced into a polymer molecule, the polymer containing this structural unit may be used as at least a part of the aforesaid polymer matrix.

Now, the onium salt structural unit (A) and the aromatic boric diester structural unit (B) are described below.

Onium Salt Structural Unit (A)

In the polymer membrane in accordance with the present invention, the onium salt structural unit (A) may be present in the form of a low-molecular-weight compound or in a form introduced into a polymer molecule. In this description, the onium salt structural units in both forms are collectively referred to as "onium salt compounds".

Onium salt compounds are compounds in which cation type atomic groups are coordinated to an atom having a lone pair, such as a nitrogen, phosphorus, sulfur, oxygen or arsenic atom. In the present invention, any well-known onium salt compound may be used. The onium salt compounds which can preferably be used in the present invention include, for example, quaternary ammonium salts, pyridinium salts, phosphonium salts, sulfonium salts, oxonium salts and arsonium salts.

As the onium salt compound becomes less soluble in sample solutions to be measured, the bicarbonate ion-sensitive membrane of the present invention can provide a longer electrode life. Accordingly, it is preferable that the solubility of the onium salt compound in water which is commonly used for sample solutions to be measured be not greater than 0.001. The term "solubility" as used herein refers to the maximum weight (g/dl) of the solute in a saturated solution at 20° C.

The onium salt compounds are more fully explained below. First of all, typical onium salt compounds are quaternary ammonium salts represented by the following formula (1):

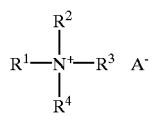 (1)

wherein $R^1$ to $R^4$ are each independently a hydrogen atom or an organic group, and $A^-$ is an anion. Compounds formed by the addition of a hydrogen ion to a primary, secondary or tertiary amine so as to produce a positive charge can also be used as quaternary ammonium salts.

In the above formula (1), no particular limitation is placed on the type of the organic groups. However, useful organic groups generally include hydrocarbon radicals such as aliphatic hydrocarbon radicals, aromatic hydrocarbon radicals and alicyclic hydrocarbon radicals; heterocyclic groups; groups formed by the attachment of —O—, —CO—, —COO—, —CONH—, —CON<, —N=CH— or the like to an end of such a hydrocarbon radical or heterocyclic group; groups formed by joining two such hydrocarbon radicals, two such heterocyclic groups, or such a hydrocarbon radical and such a heterocyclic group, by means of —O—, —CO—, —COO—, —CONH—, —CON<, —N=CH— or the like; and the like. At least one of the organic groups may be a group derived from a polymer as will be described later. The group derived from a polymer may consist of a polymer residue obtained by removing one or more atoms or groups from the polymer, and a linking group for connecting the polymer residue with the quaternary ammonium salt.

No particular limitation is placed on the number of carbon atoms present in the aliphatic hydrocarbon radicals constituting the aforesaid organic groups. However, aliphatic hydrocarbon radicals of 1 to 72 carbon atoms are generally preferred partly because the raw materials are readily available. Specific examples include branched and straight-chain alkyl groups such as methyl, ethyl, n- or isopropyl, n-, iso-, sec- or tert-butyl, pentyl, hexyl, heptyl, octyl, 2-ethylhexyl, decyl, dodecyl, tetradecyl, hexadecyl and octadecyl.

Moreover, no particular limitation is placed on the number of carbon atoms present in the aromatic hydrocarbon radicals. However, aromatic hydrocarbon radicals of 6 to 20 carbon atoms are generally preferred partly because the raw materials are readily available. Specific examples include aryl groups such as phenyl, naphthyl, xylyl, tolyl and styryl; and aralkyl groups such as benzyl and phenetyl.

Furthermore, no particular limitation is placed on the number of carbon atoms present in the alicyclic hydrocarbon radicals. However, alicyclic hydrocarbon radicals of 5 to 18 carbon atoms are preferred. Specific examples include cyclohexyl and adamantyl groups.

On the other hand, no particular limitation is placed on the number of carbon atoms and heteroatoms (e.g., oxygen, sulfur or nitrogen atoms) constituting the rings of the heterocyclic groups. However, saturated or unsaturated heterocyclic groups composed of 2 to 18 carbon atoms and 1 to 3 heteroatoms are generally preferred partly because the raw materials are readily available. Where a plurality of heteroatoms are present, they may be the same or different. Moreover, the heterocyclic groups may be condenced with a hydrocarbon rings. Specific examples of such heterocyclic groups include, for example, groups derived from heterocyclic compounds having one heteroatom, such as furan, thiophene, pyrrole and pyridine; groups derived from heterocyclic compounds having two hetero-atoms, such as thiazole, imidazole and pyrimidine; groups derived from heterocyclic compounds formed by the condensation of a heterocycle and a hydrocarbon ring, such as indole and quinoline; and groups derived from heterocyclic compounds condensation by the condensation of heterocycles, such as purine and pteridine.

The quaternary ammonium salt used in the present invention should preferably have low solubility in water, because the resulting bicarbonate ion-sensitive membrane can provide a longer electrode life. For this reason, it is preferable that at least one of $R^1$ to $R^4$ in the foregoing formula (1) be a group derived from a polymer or an organic group of 5 to 72 carbon atoms. It more preferable that at least two of $R^1$ to $R^4$ be organic groups of 5 to 72 carbon atoms.

Although the above-described organic groups may have various substituents, it is desirable that the number of highly polar substituents (e.g., hydroxyl and amino) is as small as possible in order to minimize solubility in water. Moreover, from the viewpoint of the life of the bicarbonate ion-sensitive membrane, it is desirable that the organic groups have essentially no highly active substituents (e.g., halogen, mercapto and amino) or, even if the organic groups have such substituents, their content is as low as possible.

Where the organic groups in the above formula (1) are not groups derived from a polymer, organic groups represented by the following formulae (2a) to (2c) are preferred from the viewpoint of the easy availability of raw materials and yield in the synthesis of quaternary ammonium salts.

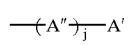

(2a)

(2b)

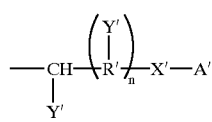

(2c)

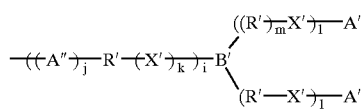

wherein A' is a monovalent aliphatic hydrocarbon radical that may have an ether linkage, or a monovalent aromatic hydrocarbon radical that may have an ether linkage; A" is a divalent aliphatic hydrocarbon radical that may have an ether linkage, or a divalent aromatic hydrocarbon radical that may have an ether linkage, Y' is a hydrogen atom or —R'—X'—A', B' is —N<, —CH< or

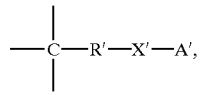

R' is a divalent or trivalent aliphatic hydrocarbon radical or aromatic hydrocarbon radical, X' is —O—, —CO—, —COO— or —CONH—; i, j, k, l, m and n are each 0 or 1; when a plurality of R' radicals are present in one organic group, the plurality of R' radicals may be the same or different; and the same shall apply to X' and A'.

Examples of the aliphatic hydrocarbon radicals and aromatic hydrocarbon radicals represented by A', A" and R' in the above formulae (2a) to (2c) are the same as the various groups described previously in connection with the foregoing formula (1).

Among the organic groups represented by the above formulae (2a) to (2c), especially preferred groups are given below.

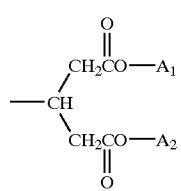

(3a)

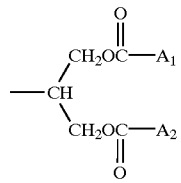

(3b)

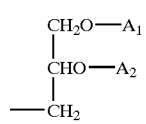

(3c)

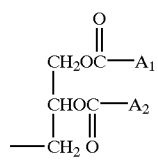

(3d)

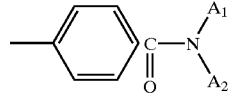

(3e)

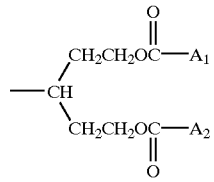

(3f)

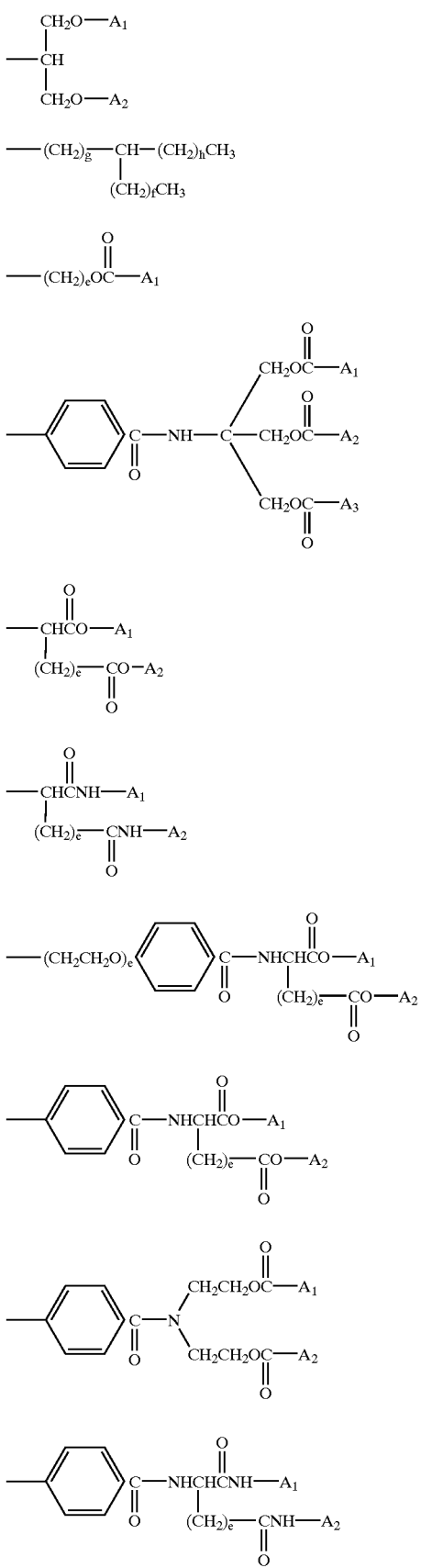

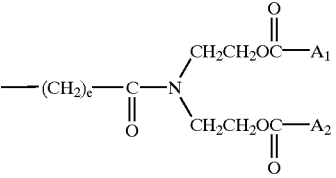

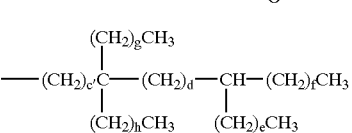

wherein $A_1$, $A_2$ and $A_3$ are each independently an aliphatic hydrocarbon radical of 8 to 30 carbon atoms which may have an ether linkage, e is an integer of 1 to 18, and c, d, f, g and h are each an integer of 0 to 36.

The quaternary ammonium salts in which at least one of the organic groups in the above formula (1) is a group derived from a polymer may be easily prepared, for example, according to any of the following processes.

(A) A process in which a quaternary ammonium salt having a reactive group is reacted with a polymer having a group capable of reacting with the reactive group.

(B) A process in which a tertiary amine serving as a precursor of a quaternary ammonium salt is reacted with a polymer having a group that forms a quaternary ammonium salt by addition to the tertiary amine.

(C) A process in which a polymer having a primary, secondary or tertiary amine serving as a precursor of a quaternary ammonium salt is reacted with a substance having a group that forms a quaternary ammonium salt by addition to the primary, secondary or tertiary amine.

(D) A process in which a quaternary ammonium salt having a polymerizable group is polymerized by a suitable means of polymerization.

(E) A process in which a primary or secondary amine serving as a precursor of a quaternary ammonium salt is reacted with a polyvalent halogenated hydrocarbon.

In the aforesaid process (A), examples of the reactive group possessed by the quaternary ammonium salt include hydroxyl, carboxyl, primary or secondary amino, and haloalkyl groups. Examples of the group on the polymer, which is capable of reacting complimentarily with these reactive groups, include haloalkyl, carboxyl, hydroxyl, and primary or secondary amino groups. As a result of the reaction between these groups, the quaternary ammonium salt is introduced into the polymer by means of a linking group such as —O—, —CO—, —COO— or —CONH—.

Examples of the polymer having a group capable of reacting with the reactive group possessed by the quaternary ammonium salt include polymethacrylic acid, polymethyl acrylate-polyhydroxyethyl methacrylate copolymer, polyhydroxyethyl acrylate-poly-hydroxyethyl methacrylate copolymer, polyacrylic acid, polyacryl-amide-polyacrylic acid copolymer, polyvinyl alcohol, polyvinyl alcohol-polyethylene copolymer, polyvinyl alcohol-polyvinyl acetate copolymer, polyepichlorohydrin, polyallylamine, polyethylene-imine, polyethylene-polymaleic anhydride copolymer, polymethyl vinyl ether-polymaleic anhydride copolymer, polystyrene-polyallyl alcohol copolymer, polystyrene-polymaleic acid copolymer, polystyrene-polymaleic anhydride copolymer, polyvinyl chloride-polyvinyl acetate copolymer, polyvinyl chloride-polyvinyl alcohol copolymer, polyvinylidene chloride-polymethyl acrylate copolymer, poly-4-vinylphenol, poly-4-vinylpyridine, poly-4-vinylpyridine-polystyrene copolymer, poly-4-vinylpyridine-polybutyl methacrylate copolymer, polyvinyl pyrrolidone-polyvinyl acetate copolymer, polychloromethylstyrene, and polychloromethylstyrene-polyhydroxyethyl methacrylate copolymer.

One specific example of the reaction between such a polymer and a quaternary ammonium salt having a reacting group is the reaction between the hydroxyl group of a hydroxyethyltrioctyl-ammonium salt and the carboxyl groups of polymethacrylic acid. Thus, there can be synthesized a polymer into which quaternary ammonium salt groups of the following formula (4) have been introduced by means of an ester linkage (—COO—).

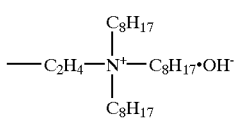
(4)

In the aforesaid process (B), the tertiary amine serving as a precursor of a quaternary ammonium salt is a compound of the following formula (5):

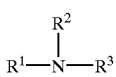
(5)

wherein $R^1$ to $R^3$ are organic groups as defined above. The group that forms a quaternary ammonium salt by addition to the tertiary amine may preferably comprise, for example, a haloaralkyl group (e.g., chlorobenzyl) or a haloalkyl group (e.g., chloromethyl).

One specific example of the aforesaid process (B) is the reaction between a chloromethylstyrene-hydroxyethyl acrylate copolymer and trioctylamine. Thus, there can be obtained a styrene-hydroxyethyl acrylate copolymer into which quaternary ammonium salt groups of the following formula (6) have been introduced.

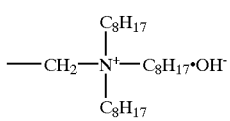
(6)

In the aforesaid process (C), examples of the polymer having a primary, secondary or tertiary amine include polyallylamine and polyethylene-imine. As the substance having a group that forms a quaternary ammonium salt by addition to the primary, secondary or tertiary amine, there may preferably be used a halobenzyl group, a haloalkyl group or the like. One specific example of the aforesaid process (C) is the reaction between polyallylamine and 1-bromooctadecane. Thus, there can be obtained a quaternary ammonium salt-containing polymer in which at least some of the amino groups present in polyallylamine have been altered to groups of the following formula (8):

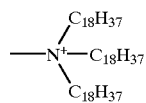
(8)

In the aforesaid process (D), the polymerizable group may be a vinyl group or the like. Such polymerizable groups may be polymerized by a means of polymerization such as radical polymerization. As a specific example, N,N-dioctadecyl-N-methyl-N-(styryl-methyl)ammonium chloride may be homopolymerized by radical polymerization in the presence of a radical polymerization initiator such as azobisisobutyronitrile or benzoyl peroxide. Moreover, quaternary ammonium salts having such a polymerizable group may also be polymerized, for example, by radical copolymerization reaction with hydroxyethyl acrylate or N-methylolacrylamide.

In the aforesaid process (E), the primary or secondary amine serving as a precursor of a quaternary ammonium salt is a compound of the following formula (9) or (10):

(9)

(10)

wherein $R^1$ and $R^2$ are each independently an organic groups as described previously. One specific example of the reaction between such a primary or secondary amine and a polyvalent halogenated hydrocarbon is the reaction between dioctylamine and 1,4-dibromo-butane.

No particular limitation is placed on the molecular weight of the quaternary ammonium salts prepared in the above-described manner and having the form of a polymer. However, from the viewpoint of formability into a membrane material, and the like, it is generally preferable that the quaternary ammonium salts have a number-average molecular weight in the range of 5,000 to 10,000,000, more preferably 10,000 to 10,000,000, and most preferably 20,000 to 10,000,000.

The quaternary ammonium salts in which one of the organic groups in the foregoing formula (1) is a group derived from a polymer include quaternary ammonium salts represented by the following general formulae (11a), (11b) and (11c):

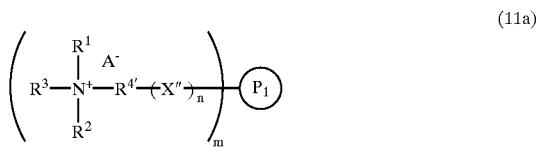
(11a)

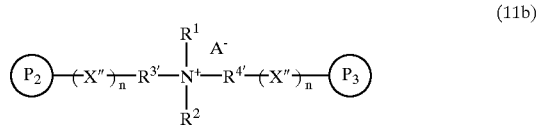
(11b)

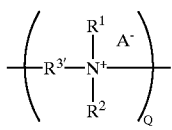
(11c)

wherein $R^1$ to $R^3$ and $A^-$ have the same meanings as defined above, $R^{3'}$ and $R^{4'}$ are each independently a divalent organic group, X" is a linking group such as —O—, —CO—, —COO— or —CONH—,

is a residue obtained by removing m groups or atoms from the polymer,

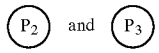

are each independently a residue obtained by removing one group or atom from the polymer, m is an integer of 1 or greater, n is 0 or 1, and Q is an integer of 1 or greater.

When the above formulae (11a) and (11b) are compared with the foregoing formula (1), it can be seen that

in the above formula (11a) corresponds to —$R^4$ in formula (1), and

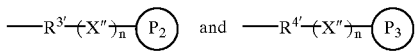

in the above formula (11b) correspond to —$R^3$ and —$R^4$, respectively, in formula (1).

As the polymer residues

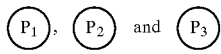

in the above formulae (11a) and (11b), resides derived from homopolymers or copolymers containing repeating units represented by the following formula (12a), (12b) or (12c) are preferred.

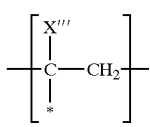
(12a)

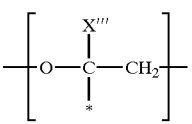
(12b)

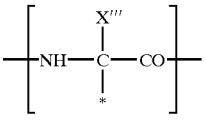
(12c)

wherein X''' is a hydrogen atom, a fluorine atom, a chlorine atom, an alkyl group of 1 to 6 carbon atoms, or a cyano group, and this group can be joined to a quaternary ammonium salt by a bond marked with an asterisk (*). The plurality of X''' radicals may be the same or different from each other.

Besides the above-described quaternary ammonium salts, pyridinium salts, phosphonium salts and sulfonium salts can also be used as onium salt compounds in the present invention. The pyridinium salts, phosphonium salts and sulfonium salts which can preferably be used in the present invention include compounds of the following formulae (13) to (15).

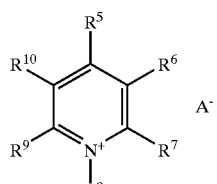
(13)

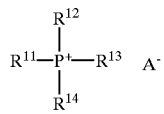
(14)

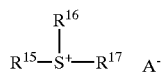
(15)

wherein $R^5$ to $R^{17}$ are each independently a hydrogen atom or an organic group, and $A^-$ is an anion.

The aforesaid organic groups can be the same as the organic groups described in connection with the foregoing formula (1). In each of the above formulae (13) to (15), at least one of the organic groups may be a group derived from a polymer as described previously. Similarly to the previously described quaternary ammonium salts, it is also preferable in the aforesaid pyridinium salts, phosphonium salts and sulfonium salts that one of the organic groups in formulae (13) to (15) is a group derived from a polymer, or these onium salt compounds have one or more, more preferably two or more, organic groups of 5 to 72 carbon atoms, because they have low solubility in water and can hence enhance the durability of the resulting electrode. Moreover, the aforesaid organic groups may have various substituents. However, in order to minimize solubility in water, it is desirable that the organic groups have neither highly active substituents (e.g., halogen, mercapto and amino) nor highly polar substituents (e.g., hydroxyl and amino), or even if the organic groups have such substituents, their content is as low as possible.

Preferred examples of the organic groups in the above formulae (13) to (15) are the groups represented by the foregoing formulae (2a) to (2c) and, in particular, the groups represented by formulae (3a) to (3r).

Aromatic Boric Diester Structural Unit (B)

In the polymer membrane in accordance with the present invention, the aromatic boric diester structural unit (B) may be present in the form of a low-molecular-weight compound or in a form introduced into the polymer molecule. In the present description, the aromatic boric diester structural units in both forms are collectively referred to as "aromatic boric diester compounds".

By allowing an aromatic boric diester compound to coexist with the above-described onium salt compound in the polymer membrane, the polymer membrane can exhibit excellent selectivity to bicarbonate ion (hydrogencarbonate ion) when it is used as an anion-sensitive membrane.

The aromatic boric diester compounds which can be used in the present invention include compounds of the following formula (16).

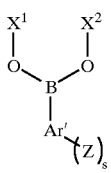
(16)

wherein $X^1$ and $X^2$ are each independently an organic group, or $X^1$ and $X^2$ are combined with the atoms adjacent thereto so as to form a ring structure, Ar' is an aromatic hydrocarbon radical, Z is a hydrogen atom or an organic group, and s is an integer of 1 or greater.

The explanation previously given for the organic groups represented by $R^1$ to $R^4$ in the foregoing formula (1) is directly applicable to the organic groups represented by $X^1$, $X^2$ and/or Z in the above formula (16). Similarly to $R^1$ to $R^4$, the organic groups represented by $X^1$, $X^2$ and/or Z may also be groups derived from a polymer.

Moreover, where $X^1$ and $X^2$ contain a polymerizable double bond, the aromatic boric diester compound may be in the form of a polymer consisting of repeating units derived from the above formula (16). In this case, the repeating units connected to the unit of interest derived from formula (16) are regarded herein as "organic groups" for convenience sake.

The organic groups represented by $X^1$, $X^2$ and/or Z in the above formula (16) may have one or more substituents. Such substituents include, for example, halogen, nitro, cyano, hydroxyl, mercapto, amino and imino. Although there is no limit to the number of substituents, it is preferable from the viewpoint of ease of synthesis, low solubility in water, and the like that the number of highly active substituents (e.g., halogen, mercapto and amino) and highly polar substituents (e.g., hydroxyl and amino) be as small as possible.

Where $X^1$ and $X^2$ in the above formula (16) are combined with the atoms adjacent thereto so as to form a ring structure, the ester moiety of the aromatic boric diester compound is less susceptible to hydrolysis. Moreover, the bicarbonate ion-sensitive membrane of the present invention provides a more stabilized electric potential response and, furthermore, has good compatibility with polymers having a membrane-forming ability as will be described later. Consequently, this membrane is preferable in that it has the advantage of providing a long electrode life.

Thus, the aromatic boric diester compounds which can preferably be used in the present invention include compounds of the following formula (17):

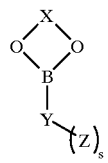
(17)

in which X is a divalent organic group of two or more carbon atoms, and Ar', Z and s have the same meanings as defined for the above formula (16).

Where X in the above formula (17) has a polymerizable unsaturated group (e.g., a vinyl group) as a pendant side chain, the compound of the above formula (17) may also be present in the form of a polymer which is formed by the polymerization of two or more molecules of the compound and hence consists of repeating units of the following formula (18):

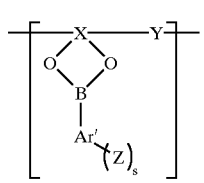
(18)

wherein Y is a group derived from a compound having a group copolymerizable with the polymerizable unsaturated group possessed by X, X has the same meaning as defined for the above formula (17), and Ar', Z and s have the same meanings as defined for the foregoing formula (16).

In the above formulae (17) and (18), it is preferable from the viewpoint of stability that the ring formed by X and a boric diester moiety (—O—B—O—) be a five-membered or six-membered ring, i.e., the numer of atoms constituting that part of the ring which is formed by X be 2 or 3. Among others, it is most preferable from the viewpoint of easy availability of raw materials, yield in synthesis, and the like that X be an ethylene or trimethylene group which may have one or more substituents.

Specific examples of X include groups represented by the following formulae (19a) and (19b):

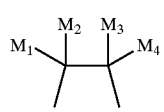
(19a)

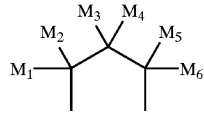
(19b)

wherein $M_1$, $M_2$, $M_3$, $M_4$, $M_5$ and $M_6$ are each independently a hydrogen atom or an organic group.

Examples of the organic groups represented by $M_1$ to $M_6$ in the above formulae (19a) and (19b) include aliphatic hydrocarbon radicals such as methyl, ethyl, propyl, isopropyl, n-butyl, isobutyl, octyl, decyl, dodecyl, tetradecyl, hexadecyl and octadecyl; aromatic hydrocarbon radicals such as phenyl, naphthyl, xylyl and benzyl; alicyclic hydrocarbon radicals such as cyclohexyl and adamantyl; heterocyclic groups derived from furan, thiophene, pyrrole, pyridine and like rings; and groups formed by joining these groups to each other by means of —O—, —CO—, —COO—, —CONH—, —CON< or —N=CH—. Moreover, at least one of the organic groups represented by $M_1$ to $M_6$ may be a group derived from a polymer. Among these organic groups, a hydrogen atom and strach-chain or branched aliphatic hydrocarbon radicals of 1 to 36 carbon atoms are especially preferred from the viewpoint of ease of synthesis.

The divalent organic groups of two or more carbon atoms which are represented by X in the above formula (17) and are especially preferred for use in the present invention include groups represented by the following formulae (20a) to (20s):

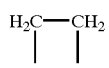
(20a)

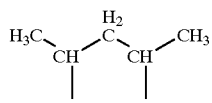
(20b)

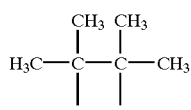
(20c)

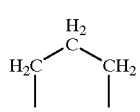
(20d)

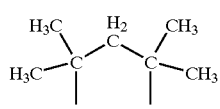
(20e)

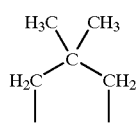
(20f)

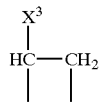
(20g)

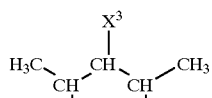
(20h)

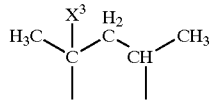
(20i)

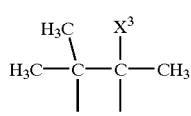
(20j)

-continued

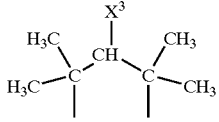
(20k)

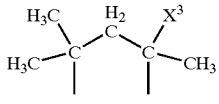
(20l)

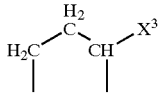
(20m)

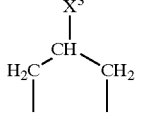
(20n)

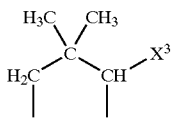
(20o)

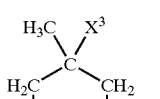
(20p)

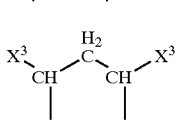
(20q)

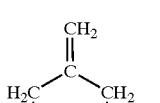
(20r)

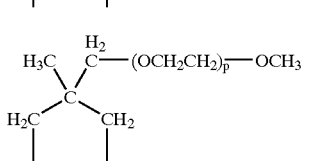
(20s)

wherein $X^3$ is an aliphatic hydrocarbon radical or a group derived from a polymer; when a plurality of $X^3$ radicals are present in the same structure, they may be different from each other; and p is an integer of 1 to 4.

As the group derived from a polymer which is represented by $X^3$, there may be used any of the groups derived from a polymer which were previously described in connection with the organic groups in the quaternary ammonium salts of the foregoing formula (1).

Examples of the aromatic hydrocarbon radical represented by Ar' in the foregoing formulae (16) to (18) include groups derived from aromatic hydrocarbon rings of 6 to 10 carbon atoms, such as benzene, toluene, xylene and naphthalene rings. Among others, the aromatic boric diester compounds in which Ar' is an aromatic hydrocarbon radical derived from a benzene or naphthalene ring are especially preferred because they show a good yield in the synthesis thereof Moreover, these aromatic boric diester compounds themselves have improved stability and consequently provide a stabilized electric potential response.

Although the aromatic hydrocarbon radical may have one or more substituents other than Z, it is preferable from the viewpoint of yield in synthesis and the like that the number of substituents is as small as possible. Preferred substituents include, for example, a halogen atom (e.g., chlorine), a nitrile group and a nitro group. Moreover, the preferred number of substituents is 2 or less.

In the above formulae (16) to (18), Z is a hydrogen atom or an organic group. Examples of the organic group include aliphatic hydrocarbon radicals such as methyl, ethyl, propyl, isopropyl, n-butyl, isobutyl, octyl, decyl, dodecyl, tetradecyl, hexadecyl and octadecyl; aromatic hydrocarbon radicals such as phenyl, naphthyl, xylyl and benzyl; alicyclic hydrocarbon radicals such as cyclohexyl and adamantyl; heterocyclic groups derived from furan, thiophene, pyrrole, pyridine and like rings; and groups formed by combining these groups with —O—, —CO—, —COO—, —CONH—, —CON< or —N=CH—. Moreover, the organic group may be a group derived from a polymer.

The aromatic boric diester compounds in which, among these organic groups, Z is a group containing an unsubstituted or substituted brahched or straight-chain hydrocarbon radical of 1 to 72 carbon atoms are preferred because they show an improvement in compatibility with polymers having a membrane-forming ability as will be described later. Moreover, the aromatic boric diester compounds in which Z is a brahched or straight-chain alkyl group of 1 to 72 carbon atoms having —O—, —CO—, —COO—, —CONH—, —CON< or —N=CH— are preferred because raw materials for the synthesis thereof are readily available and they show a good yield in the systhesis thereof.

Where the aromatic hydrocarbon radical represented by Ar' is a phenylene group, Z in the above formulae (16) and (17) can be attached to the o-, n- or p-pisition with respect to the boron atom. Where the aromatic hydrocarbon radical represented by Ar' is a naphthyl group, Z can be attached to any of the carbon atoms located at the 1- to 8-positions.

No particular limitation is placed on the number (s) of Z radicals attached to Ar'. However, from the viewpoint of yield in synthesis, and the like, s is preferably in the range of 1 to 3.

The groups which are represented by Z and can preferably be used in the present invention include, for example, groups represented by the following formulae (21a) to (21j):

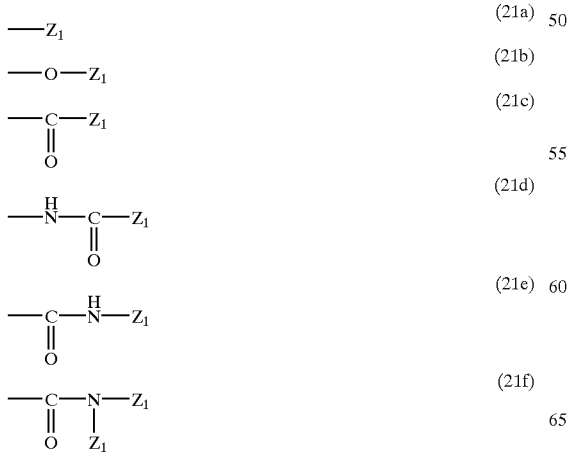

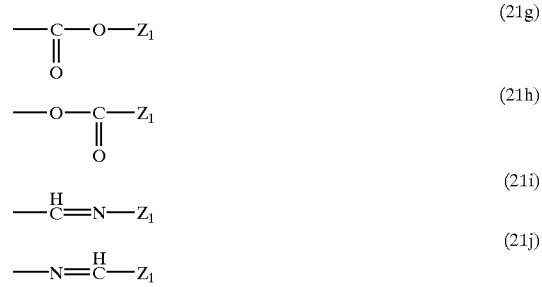

wherein $Z_1$ is an aliphatic hydrocarbon radical of 1 to 72 carbon atoms, a group formed by joining two aliphatic hydrocarbon radicals to each other by means of —O—, —CO— or —COO—, or —CH$_2$(OCH$_2$CH$_2$)$_n$—OCH$_3$ (in which n is an integer of 1 to 10).

As $Z_1$ in the above formulae (21a) to (21j), there may be used a group suitably chosen from the groups of formulae (3a) to (3r) which were previously described in connection with the quaternary ammonium compounds of formula (1).

In an especially preferred embodiment of the present invention, $Z_1$ in the above formulae (21a) to (21j) is a bracnhed alkyl group of 8 to 18 carbon atoms. In this case, the resulting aromatic boric diester compound has excellent compatibility with polymers as will be described later, and hence provides a more stabilized electric potential response. Examples of the bracnhed alkyl group of 8 to 18 carbon atoms include 2-ethylhexyl, 3,7-dimethyloctyl, 2-butyloctyl and 2-hexyldecyl groups.

In the foregoing formula (17), the groups represented by X, Ar' and Z may be any combination of groups. However, with consideration for the stability of the bicarbonate ion-sensitive membrane of the present invention, selectivity to hydrogencarbonate ion, yield in synthesis, easy availability of raw materials, and the like, aromatic boric diester compounds of the following formulae (22a) and (22b) are especially preferred.

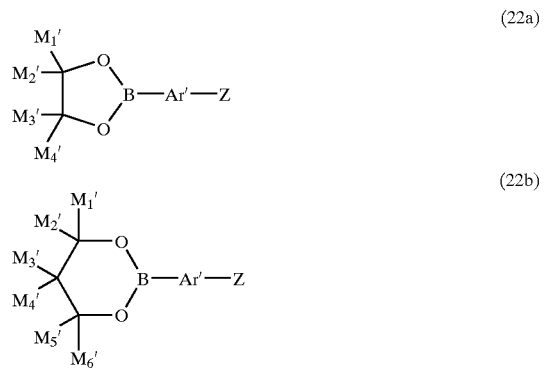

wherein $M_1'$, $M_2'$, $M_3'$, $M_4'$, $M_5'$ and $M_6'$ are each independently a hydrogen atom, a methyl group, or a group derived from a polymer, Ar' is an aromatic hydrocarbon radical, and Z is any of the groups of the above formulae (21a) to (21j).

The aromatic boric diester compounds which can be used in the present invention may be synthesized according to any of per se known processes. However, the following exemplary process of synthesis can preferably be employed.

First of all, an aromatic boric acid compound is synthesized by reacting a bromoaryl compound with a trialkoxyborane in the presence of n-butyllithium. Then, this aromatic boric acid compound is converted into a cyclic diester of the aromatic boric acid by reacting it with a low-molecular-weight diol compound such as ethylene glycol or propanediol, or a high-molecular-weight diol compound such as polyvinyl alcohol or a compound obtained by functionalizing some hydroxyl groups of a high-molecular-weight diol compound such as polyvinyl alcohol (e.g., by esterification). Furthermore, the desired aromatic boric diester compound can be purified from the reaction mixture by column chromatography using silica gel particles as the stationary phase, or by distillation, recrystallization or the like. As the developing solvent for this purpose, well-known solvents such as chloroform, acetone and methanol may be used alone or in admixture of two or more.

Where an aromatic boric diester having a high molecular weight is desired, the aromatic boric diester compound can be obtained in the form of a homopolymer or copolymer, for example, by preparing a cyclic ester of an aromatic boric acid having a polymerizable group (e.g., 4-vinylphenylboric acid) according to the above-described process and then polymerizing this ester compound alone, or by copolymerizing the aforesaid ester compound with another compound having polymerizability. These polymeric compounds may be easily synthesized by employing any polymerization technique that is suitably chosen from the common polymerization techniques for the synthesis of polymers (e.g., radical polymerization, cationic polymerization, and anionic polymerization), according to the compound used. Generally, radical polymerization in the presence of a radical initiator (e.g., azobisisobutyronitrile) is especially preferred because of the ease of control of the polymer structure, the convenience of polymerization, and the like. The desired aromatic boric diester compound can be obtained by purifying the resulting polymeric compound by column chromatography using silica gel particles as the stationary phase, or by a suitable means such as distillation or recrystallization. As the developing solvent for this purpose, well-known solvents such as chloroform, acetone and methanol may be used alone or in admixture of two or more.

The purity of an aromatic boric diester compound can be confirmed by analysis using thin-layer chromatography (hereinafter abbreviated as TLC). Silica gel or alumina is suitably used as the support for TLC analysis. As the developing solvent, well-known solvents such as chloroform, acetone and methanol may be used alone or in admixture of two or more. Moreover, the structure of an aromatic boric diester can be determined by using proton NMR spectroscopy suitably in combination with elemental analysis or gel permeation chromatography.

In a specific embodiment of the above-described aromatic boric diester compound, there is a compound in which an onium salt structural unit (A), particularly a quaternary ammonium salt structural unit, coexists with an aromatic boric diester structural unit (B) in one molecule. This compound, when used alone, can produce a similar effect to that of a mixture of an onium salt compound and an aromatic boric diester compound. Specific examples of this compound include aromatic boric diester compounds of the following formulae (23) to (25):

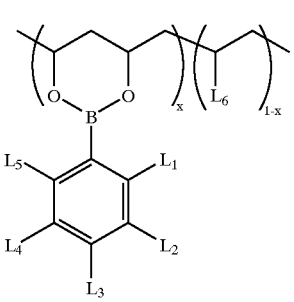

(23)

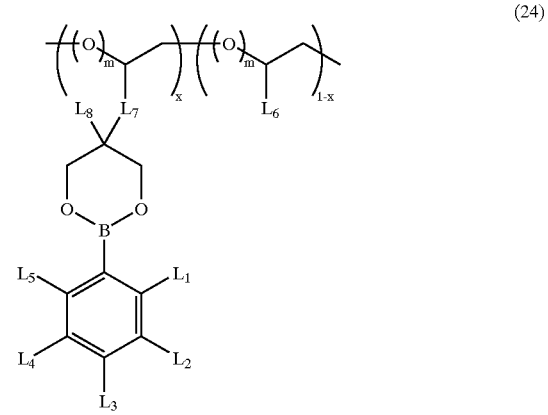

(24)

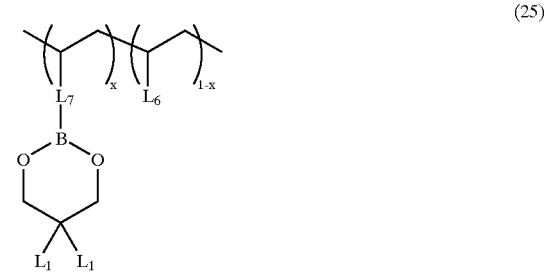

(25)

wherein at least one of $L_1$ to $L_5$ is a branched or straight-chain alkyl group of 1 to 72 carbon atoms which may have —O—, —CO—, —COO—, —CONH—, —CON< or —N=CH—, and the others are hydrogen atoms; $L_6$ is a group containing a quaternary ammonium salt group; $L_7$ is a divalent organic group of 1 to 8 carbon atoms; $L_8$ is a hydrogen atom or an alkyl group of 1 to 3 carbon atoms; m is 0 or 1; and $0 < x \leq 1$. It is to be understood that the repeating units whose proportions are designated by x and 1−x may be present alternately, randomly or in blocks.

Examples of the branched or straight-chain alkyl group of 1 to 72 carbon atoms represented by $L_1$ to $L_5$ in the above formulae include methyl, ethyl, propyl, 2-ethylhexyl, dodecyl, tetradecyl and octadecyl. Examples of the branched or straight-chain alkyl group of 1 to 72 carbon atoms having —O—, —CO—, —COO—, —CONH—, —CON< or —N=CH— include methoxy, ethoxy, propoxy, 2-ethylhexyloxy, dodecyloxy, tetradecyloxy and octadecyloxy.

Examples of the group represented by $L_6$ include groups derived from quaternary ammonium salts of the foregoing formula (1). Examples of the divalent organic group represented by $L_7$ include aliphatic hydrocarbon radicals such as methylene, ethylene, trimethylene, tetramethylene, pentamethylene, hexamethylene, heptamethylene, octamethylene and propylene; aromatic hydrocarbon radicals such as phenylene and naphthylene; and groups obtained by joining similar or different ones of these groups by means of —O—, —CO—, —COO—, —CONH—, —CON< or —N=CH—.

Examples of the alkyl group of 1 to 3 carbon atoms represented by $L_8$ include methyl, ethyl and propyl.

x may be greater than 0 and not greater than 1. However, in order to enhance selectivity to bicarbonate ion, it is especially preferably that x be in the range of 0.2 to 1.0.

No particular limitation is placed on the molecular weights of the aromatic boric diester compounds of the above formulae (23) to (25). However, in order to obtain aromatic boric diester compounds having a sufficient membrane-forming ability by themselves, it is generally preferable that they have a number-average molecular weight in the range of 5,000 to 1,000,000,000 and more preferably 5,000 to 10,000,000.

Among the boric diester compounds represented by the above formulae (23) to (25), the aromatic boric diester compounds in which one of $L_1$ to $L_5$ is a 2-ethylhexyloxy, dodecyloxy, tetradecyloxy or octadecyloxy group and the others are hydrogen atoms, $L_6$ is a N,N,N,N-(oxycarbonylethyl)dioctadecylmethylammonium, N,N,N-(oxycarbonylmethyl)dioctadecylmethylammonium, N,N,N,N-(carbonyloxyethyl)dioctadecylmethylammonium or N,N,N,N-(p-benzyl)-dioctadecylmethylammonium group, $L_7$ is an oxymethylene, methyleneoxymethylene, carbonyloxymethylene or phenylene group, $L_8$ is a hydrogen atom or a methyl group, and x is in the range of 0.9 to 0.5 are especially preferred from the viewpoint of formability into a membrane, ease of synthesis, and the like.

Bicarbonate Ion-sensitive Membrane

The bicarbonate ion-sensitive membrane of the present invention may comprise a polymer membrane containing the above-described onium salt structural unit (A) and aromatic boric diester structural unit (B) in the formed of low-molecular-weight compounds dispersed in the polymer or in a form introduced into a polymer molecule.

In one embodiment, the sensitive membrane of the present invention may contain an onium salt compound and an aromatic boric diester compound in a form dispersed in a suitable polymer matrix.

However, where one or both of the onium salt compound and the aromatic boric diester compound are membrane-forming polymers, at least a part, or essentially all in some cases, of the polymer matrix may be omitted. Whether the use of the polymer matrix should be omitted or not may be suitably determined on the basis of the properties required of the sensitive membrane, and the like.

Thus, examples of the bicarbonate ion-sensitive membrane of the present invention include:

① a membrane comprising a polymer matrix in which a low-molecular-weight onium salt compound and a low-molecular-weight aromatic boric diester compound are dispersed;

② a membrane comprising a low-molecular-weight onium salt compound and a high-molecular-weight (polymeric) aromatic boric diester compound, and optionally containing another polymer matrix;

③ a membrane comprising a high-molecular-weight (polymeric) onium salt compound and a low-molecular-weight aromatic boric diester compound, and optionally containing another polymer matrix;

④ a membrane comprising a high-molecular-weight (polymeric) onium salt compound and a high-molecular-weight (polymeric) aromatic boric diester compound; and ⑤ a membrane comprising a polymer in which the onium salt structural unit (A) and the aromatic boric diester structural unit (B) coexist in the same molecule.

The proportions in which the onium salt structural unit (A) and the aromatic boric diester structural unit (B) are present in the bicarbonate ion-sensitive membrane of the present invention may be suitably chosen on the basis of the performance desired for the sensitive membrane, and the like. However, these proportions should generally desirably be such that, whether the aforesaid structural units (A) and (B) are present in the form of low-molecular-weight compounds or in a form introduced into a polymer molecule, the ratio of [the number of moles of the aromatic boric diester structural unit (B)] to [the number of moles of the onium salt structural unit (A)] is at least 0.01, preferably in the range of 0.1 to 100,000, and more preferably in the range of 0.3 to 10,000.

It is desirable that the polymer which may be used as the matrix in the sensitive membrane of the present invention is a membrane-forming polymer having essentially no solubility in water, because the membrane is usually used in aqueous solutions. The polymers which can be used in the present invention include, for example, homopolymers or copolymers of vinyl halides such as vinyl chloride, vinyl bromide and vinylidene chloride; homopolymers or copolymers of unsubstituted and substituted styrenes such as styrene, chlorostyrene and bromostyrene; homopolymers or copolymers of acrylic and methacrylic esters such as methyl acrylate, ethyl acrylate, ethyl methacrylate and butyl methacrylate; homopolymers or copolymers of vinyl esters such as vinyl acetate; polymers of dienes such as butadiene and isoprene, and copolymers of such a diene and styrene, acrylonitrile or the like; polyurethanes; siloxane polymers or copolymers; and cellulose derivatives such as cellulose acetate and cellulose nitrate. These polymers may be used alone or in admixture of two or more.

Among the above-described membrane-forming polymers, homopolymers or copolymers of vinyl halides and siloxane polymers or copolymers are especially preferred because they can provide a longer life to the bicarbonate ion-sensitive membrane of the present invention when it is used in biological fluids.

Where a polymer matrix as described above is used in the sensitive membrane of the present invention, the contents of the onium salt compound and the boric diester compound in the sensitive membrane may vary according to the end use of the sensitive membrane, and the like. However, it is generally preferable to use the polymer matrix in an amount of 1 to 70 parts by weight, more preferably 1 to 60 parts by weight, and most preferably 1 to 50 parts by weight, per 100 parts by weight of the combined amount of the onium salt compound, the aromatic boric diester compound and the polymer matrix.

Moreover, a fat-soluble anion salt may preferably be incorporated into the bicarbonate ion-sensitive membrane of the present invention as required. This makes it possible to further improve the response speed to ions of the sensitive membrane of the present invention and measure the ion concentrations in samples more rapidly. To this end, the fat-soluble anion preferably comprises one which has a negatively charged atomic group in the molecule and which is soluble in organic solvents such as chloroform and hexane. This fat-soluble anion is used as a salt formed from the fat-soluble anion and a counter cation.

The fat-soluble anion salt should preferably have low solubility in water, because the resulting anion-sensitive membrane has a longer life. It is preferable that the solubility in water of the fat-soluble anion salt used in the present invention be not greater than 10, more preferably not greater than 1, and most preferably not greater than 0.01. The term "solubility" as used herein refers to the maximum weight (g/dl) of the solute present in a saturated solution of a fat-soluble anion sodium salt at 20° C.

The fat-soluble anion salts which can be used in the present invention include, for example, tetraphenyl borates such as tetrakis[3,5-bis(trifluoromethyl)phenyl]borate, tetrakis(4-chlorophenyl)borate, tetrakis(4-fluorophenyl) borate and tetraphenyl borate; salts of long-chain alkylsulfonic acids such as decylsulfonic acid, dodecylsulfonic acid, dodecylbenzenesulfonic acid, octadecylsulfonic acid and oleylsulfonic acid; salts of long-chain dialkylsulfosuccinic acids such as bismethylhexylsulfosuccinic acid, dioctylsulfosuccinic acid, didecylsulfosuccinic acid and didodecylsulfosuccinic acid; salts of long-chain alkylphosphonic acids such as decylphosphonic acid, dodecylphosphonic acid, dodecylbenzenephosphonic acid, octadecylphosphonic acid and oleylphosphonic acid; salts of long-chain dialkylphosphonic acids such as bismethylhexylphosphonic acid, dioctyiphosphonic acid, didecylphosphonic acid and didodecylphosphonic acid; and salts of long-chain dialkylphosphosuccinic acids such as bismethylhexylphosphosuccinic acid, dioctylphosphosuccinic acid, didecylphosphosuccinic acid and didodecylphosphosuccinic acid. Among the above-described fat-soluble anion salts, tetraphenyl borates are preferably used because they have low solubility in water and can hence provide electrode having high durability.

As the counter cation for the aforesaid fat-soluble anion, any well-known cation may be used without limitation. However, potassium and sodium ions are preferred because they have good solubility in an organic solvent used for membrane formation.

No particular limitation is placed on the content of the fat-soluble anion salt in the sensitive membrane of the present invention. However, if the molar ratio of the fat-soluble anion salt based on the onium salt compound [i.e., (the number of moles of the fat-soluble anion salt)/(the number of moles of the onium salt compound)] is less than 0.01, the addition of the fat-soluble anion salt will produce no effect. If it is greater than 1, the resulting membrane will show a reduction in responsivity to ions and may sometimes lose its responsivity to ions. Accordingly, it is generally preferable that the aforesaid molar ratio be in the range of 0.1 to 0.7 and more preferably 0.2 to 0.7.

The sensitive membrane of the present invention may be formed in substantially the same manner as the membrane formation of per se known polymers. According to one exemplary and preferred method, the onium salt compound and the aromatic boric diester compound, as well as the polymer and fat-soluble anion salt which may be added as required, are dissolved in an organic solvent. After this solution is spread or cast over a planar surface, the organic solvent is evaporated to form a membranous material.

As the aforesaid organic solvent, any organic solvent may be used without limitation, provided that it can dissolve the onium salt compound and the aromatic boric diester compound, as well as the polymer and fat-soluble anion salt which may be added as required. Specific examples of the organic solvents which can generally and preferably be used include tetrahydrofuran, dioxane, chloroform, methylene chloride, dimethylformamide, dimethylacetamide, benzene and toluene.

The membranous material obtained according to the above-described method generally comprises a transparent or white homogeneous membrane, and this membranous material can be directly used as an anion-sensitive membrane. The membrane thickness can be controlled by regulating the amounts of ingredients used and the membrane area. However, with consideration for the operability of the resulting ion-selective electrode, and the like, the membrane thickness is preferably in the range of 1 $\mu$m to 1 mm and more preferably 2 to 606 $\mu$m.

The bicarbonate ion-sensitive membrane of the present invention, which is formed in the above-described manner, can be applied to ion-selective electrodes having a well-known construction. Generally, the membrane is preferably used in an ion-selective electrode constructed by providing a vessel comprising a cylindrical electrode body fitted with the sensitive membrane in at least that part thereof which is to be immersed in a sample solution, and filling the vessel with an internal reference electrode and an internal electrolyte or ionic conductive substance. In this electrode, no particular limitation is placed on the materials of the components other than the anion-sensitive membrane, and there may be used any of per se known materials. As the internal reference electrode, there may be used, for example, an electrically conductive substance such as platinum, gold or carbon graphite, or a hardly soluble metal chloride such as silver-silver chloride or mercury-mercury chloride. As the internal electrolyte, there may preferably be used, for example, an aqueous solution of a metallic salt such as an aqueous sodium chloride solution, an aqueous potassium chloride solution or an aqueous sodium hydrogencarbonate solution. Examples of suitable ionic conductive substances include electrical conductors such as gold, platinum and graphite; and ionic conductors such as silver chloride and mercury chloride. Moreover, as the material of the cylindrical electrode body, there may be used, for example, polyvinyl chloride or polymethyl methacrylate.

A typical example of an ion-selective electrode is illustrated in FIG. 1. The ion-selective electrode of FIG. 1 is constructed by providing a vessel comprising a cylindrical electrode body 11 fitted with an anion-sensitive membrane 12 at the bottom thereof, filling the vessel with an internal electrolyte 13, and disposing an internal reference electrode 14 therein. Reference numeral 15 designates an O-ring used for liquid-tight sealing purposes.

The ion-selective electrodes to which the bicarbonate ion-sensitive membrane of the present invention can be applied are not limited to the construction illustrated in FIG. 1, but there may be used any type of ion-selective electrode having an anion-sensitive membrane. Other suitable ion-selective electrodes include, for example, ion-selective electrodes constructed by affixing the bicarbonate ion-sensitive membrane of the present invention directly to an electrical conductor (e.g., gold, platinum or graphite) or an ionic conductor (e.g., silver chloride or mercury chloride).

An ion-selective electrode utilizing the bicarbonate ion-sensitive membrane of the present invention may be used according to any of per se known methods. For example, the ion-selective electrode may be used in a manner illustrated in FIG. 2. Specifically, an ion-selective electrode 21, together with a salt bridge 22, is immersed in a sample solution 23. The other end of the salt bridge, together with an external reference electrode 24, is immersed in a saturated potassium chloride solution 26. As the aforesaid external reference electrode, there may be used any per se known electrode. Preferred examples thereof include a calomel electrode, a silver-silver chloride electrode, a platinum plate and carbon graphite.

As described above, the bicarbonate ion-sensitive membrane of the present invention is formed from a composition which comprises an onium salt compound and an aromatic boric diester compound, and may further contain a membrane-forming polymer and a fat-soluble anion salt as required. This membrane has significantly high responsivity to bicarbonate (or hydrogencarbonate) ion relative to interfering ions (e.g., sulfate, nitrate, chloride and salicylate ions) present in biological fluids such as blood and urine, and further shows a very high response speed.

Although the reason why bicarbonate (or hydrogencarbonate) ions can be specifically detected by using the bicarbonate ion-sensitive membrane of the present invention has not been clearly understood, the selective responsivility to bicarbonate ion is a phenomenon which occurs only as a result of the combined use of an aromatic boric diester compound and an onium salt compound. Accordingly, it is believed that the function of an aromatic boric diester compound as an electron-accepting substance contributes to the high selectivity to bicarbonate (or hydrogencarbonate) ion.

Consequently, the sensitive membrane of the present invention permits hydrogencarbonate ions contained in biological fluids such as blood and urine to be rapidly determined with very high accuracy.

EXAMPLES

The present invention is more specifically explained with reference to the following examples. However, these examples are not to be construed to limit the scope of the invention. The meanings of the symbols used in these examples are as follows.

Proton NMR: $^1$NMR
In NMR spectra:
  Singlet: s
  Doublet: d
  Multiplet: m
Benzene ring: phe
Salicylate ion: Sal$^-$
Polyvinyl chloride: PVC
Polyvinylidene chloride: PVdC
2-Nitrophenyl octyl ether: NPOE
Tetraoctylammonium bromide: TOABr
Trioctyltin chloride: TOTC
Tetraoctadecylammonium bromide: TOAB
Tetrakis[3,5-bis(trifluoromethyl)phenyl]borate sodium salt: TFPB
Tetrakis[4-chlorophenyl]borate potassium salt: TCPB
Sodium di(2-ethylhexyl)sulfosuccinate: DESS The various compounds used in the examples are summarized in Tables 1 to 23 below. In Tables 1 to 23, the weight-average molecular weight of a high-molecular-weight compound as determined by gel permeation chromatography is designated by MW, and the proportions of repeating units in the molecule as determined by NMR or elemental analysis are designated by x and y. It is to be understood that the repeating units whose proportions are designated by x and y may be present alternately, randomly or in blocks.

TABLE 1

| Compound No. | Structure of onium salt compound |
|---|---|
| 1 | $CH_3N^+(n\text{-}C_8H_{17})_3\ Cl^-$ |
| 2 | $(n\text{-}C_8H_{17})_4N^+\ Br^-$ |
| 3 | $(n\text{-}C_{18}H_{37})_4N^+\ Br^-$ |
| 4 | 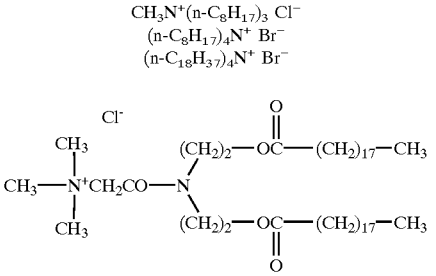 |
| 5 | 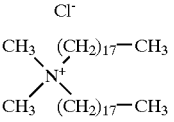 |
| 6 | 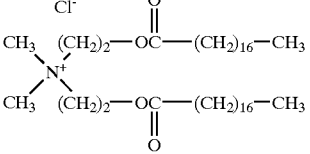 |
| 7 | 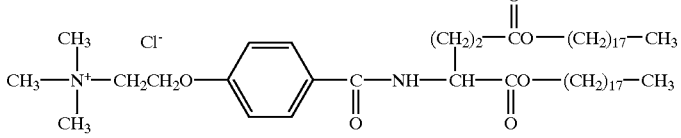 |

TABLE 1-continued

| Compound No. | Structure of onium salt compound |
|---|---|
| 8 | pyridinium-C₁₈H₃₇ Cl⁻ |

TABLE 2

| Compound No. | Structure of onium salt compound |
|---|---|
| 9 | 4-(1-butylpentyl)pyridinium derivative with N,N-bis[2-(octadecanoyloxy)ethyl] amide, Cl⁻ |
| 10 | Copolymer (x = 0.5, y = 0.5, MW = 460000) of 2-hydroxyethyl methacrylate and methacrylate bearing quaternary ammonium with N,N-bis[2-(octadecanoyloxy)ethyl] group, Cl⁻ |
| 11 | Copolymer (x = 0.5, y = 0.5, MW = 360000) of 2-hydroxyethyl methacrylate and methacrylate bearing quaternary ammonium with N,N-bis[2-(heptadecanoyloxy)ethyl]-N-methyl group, Cl⁻ |

TABLE 3

| Compound No. | Structure of onium salt compound |
|---|---|
| 12 | Copolymer of styrene (0.45) bearing benzyl-N-methyl-N,N-dioctadecyl ammonium chloride and 2-hydroxyethyl methacrylate (0.55), MW = 400000 |

TABLE 3-continued
| Compound No. | Structure of onium salt compound |
|---|---|
| 13 | 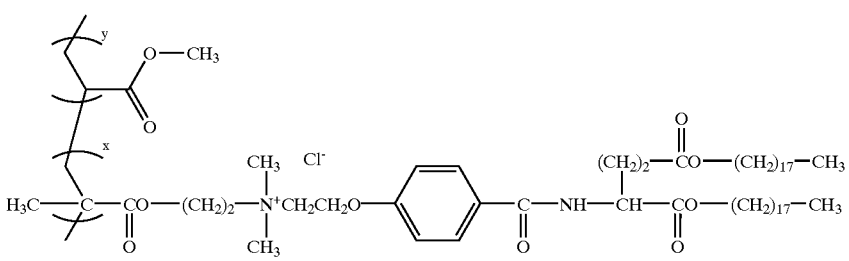<br>x = 0.5, y = 0.5, MW = 400000 |
| 14 | 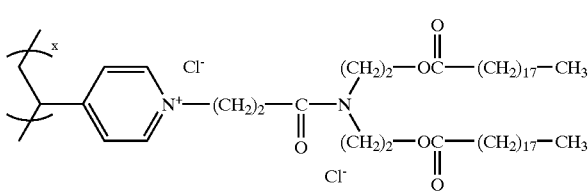<br>x ≅ 1.0, MW = 640000 |
| 15 | 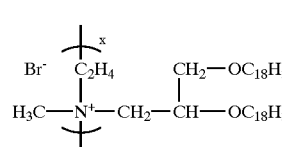<br>x ≅ 1.0, MW = 850000 |
TABLE 4
| Compound No. | Structure of onium salt compound |
|---|---|
| 16 | $(n\text{-}C_{12}H_{25})_4P^+\ Cl^-$ |
| 17 | $(n\text{-}C_{18}H_{37})_3S^+\ Cl^-$ |
| 18 | $(n\text{-}C_{18}H_{37})_4P^+\ Cl^-$ |
| 19 | 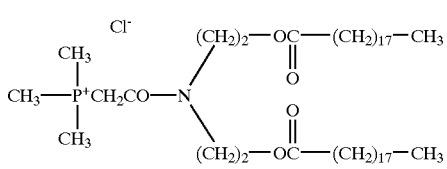 |
| 20 | 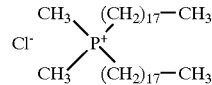 |
| 21 | 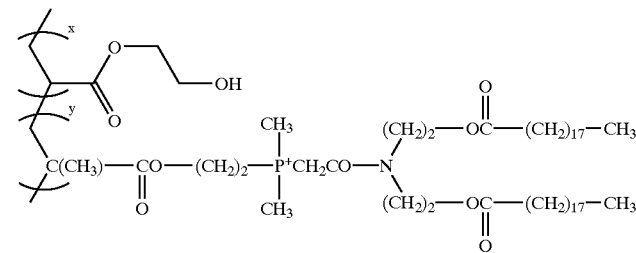<br>x = 0.5, y = 0.5, MW = 620000 |

TABLE 4-continued

| Compound No. | Structure of onium salt compound |
|---|---|
| 22 | (structure shown; x = 0.5, y = 0.5, MW = 520000) |

TABLE 5

| Compound No. | Structure of boric diester compound |
|---|---|
| 23 | (structure shown) |
| 24 | (structure shown) |
| 25 | (structure shown) |
| 26 | (structure shown) |
| 27 | (structure shown) |
| 28 | (structure shown) |

TABLE 5-continued
| Compound No. | Structure of boric diester compound |
| --- | --- |
| 29 | 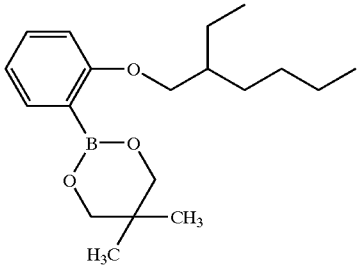 |
TABLE 6
| Compound No. | Structure of boric diester compound |
| --- | --- |
| 30 | 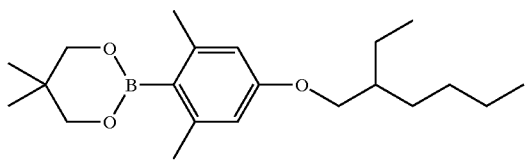 |
| 31 | 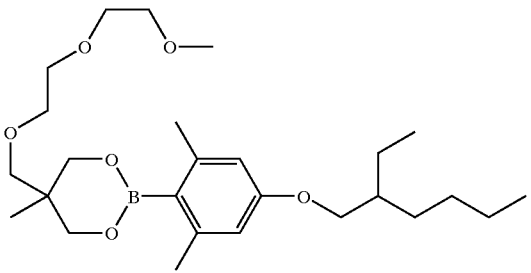 |
| 32 | 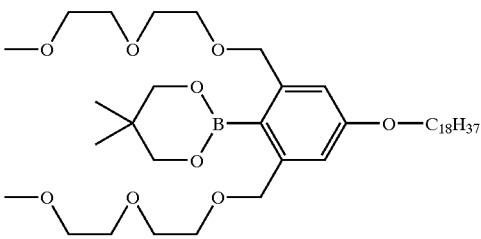 |
| 33 | 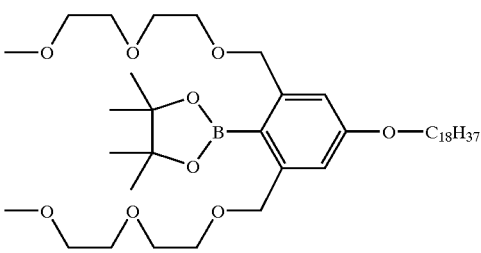 |

TABLE 7

| Compound No. | Structure of boric diester compound |
|---|---|
| 34 | Polymer with x = 0.5, y = 0.5, MW = 400000 |
| 35 | Polymer with x = 0.5, y = 0.5, MW = 420000 |

TABLE 8

| Compound No. | Structure of boric diester compound |
|---|---|
| 36 | Polymer with x ≅ 1.0, MW = 330000 |
| 37 | Polymer with x ≅ 1.0, MW = 342000 |
| 38 | Polymer with x ≅ 1.0, MW = 789000 |

TABLE 8-continued

| Compound No. | Structure of boric diester compound |
|---|---|
| 39 | (structure shown) $x \cong 1.0$, MW = 534000 |

TABLE 9

Structure of boric diester compound (structure shown)

$^1$HNMR (δ ppm): 0.8–2.2(m, alkyl-CH$_3$, alkyl-CH$_2$, alkyl-CH, OOC—CH$_2$), 3.3–3.5(m, N$^+$—CH$_3$, N$^+$—CH$_2$), 3.8–4.1(m, phe-O—CH$_2$, COO—CH), 4.6(m, BO—CH), 6.9, 7.8(bs, phe-H)

| Compound No. | x | y | MW | Elemental analysis (C %, H %, N %) | |
|---|---|---|---|---|---|
| | | | | Found values | Calculated values |
| 40 | 0.9 | 0.1 | 382000 | 71.25, 9.41, 0.69 | 71.33, 9.52, 0.41 |
| 41 | 0.7 | 0.3 | 568000 | 71.27, 10.16, 1.14 | 71.04, 10.35, 0.99 |
| 42 | 0.5 | 0.5 | 728000 | 70.59, 10.88, 1.24 | 70.84, 10.91, 1.38 |

TABLE 10

Structure of boric diester compound

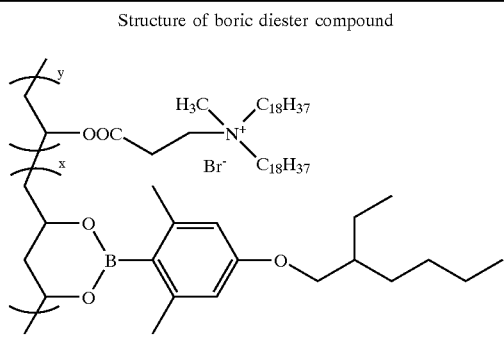

$^1$HNMR (δ ppm): 0.8–2.3(m, alkyl-CH$_3$, alkyl-CH$_2$, alkyl-CH, OOC—CH$_2$, phe-CH$_3$), 3.3–3.5(m, N$^+$—CH$_3$, N$^+$—CH$_2$), 3.8–4.0(m, phe-O—CH$_2$, COO—CH), 4.6(m, BO—CH), 6.5(bs, phe-H)

| Compound No. | x | y | MW | Elemental analysis (C %, H %, N %) | |
|---|---|---|---|---|---|
| | | | | Found values | Calculated values |
| 43 | 0.9 | 0.1 | 423000 | 72.55, 9.76, 0.51 | 72.31, 9.84, 0.38 |
| 44 | 0.7 | 0.3 | 592000 | 71.88, 10.28, 1.13 | 71.68, 10.52, 0.94 |
| 45 | 0.5 | 0.5 | 732000 | 70.99, 10.74, 1.25 | 71.24, 11.00, 1.34 |

TABLE 11

Structure of boric diester compound

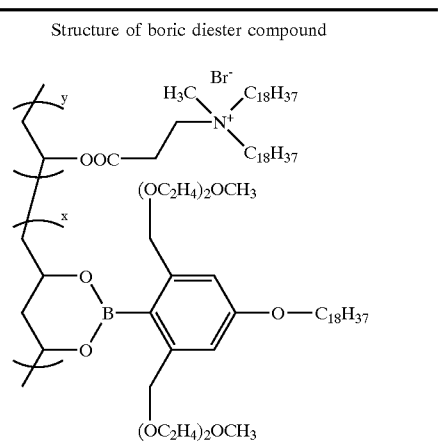

$^1$HNMR (δ ppm): 0.8–1.5(m, alkyl-CH$_3$, alkyl-CH$_2$), 2.2(t, OOC—CH$_2$), 3.3–4.0(m, N$^+$—CH$_3$, N$^+$—CH$_2$, phe-O—CH$_2$, O—CH$_2$CH$_2$—O, O—CH$_3$, COO—CH), 4.6(m, BO—CH, phe-CH$_2$), 6.8(s, phe-H)

| Compound No. | x | y | MW | Elemental analysis (C %, H %, N %) | |
|---|---|---|---|---|---|
| | | | | Found values | Calculated values |
| 46 | 0.9 | 0.1 | 740000 | 68.16, 10.19, 0.50 | 68.23, 10.22, 0.20 |
| 47 | 0.7 | 0.3 | 852000 | 69.00, 10.48, 0.89 | 68.75, 10.56, 0.59 |
| 48 | 0.5 | 0.5 | 952000 | 68.98, 11.12, 1.20 | 69.26, 10.90, 0.99 |

TABLE 12

Structure of boric diester compound

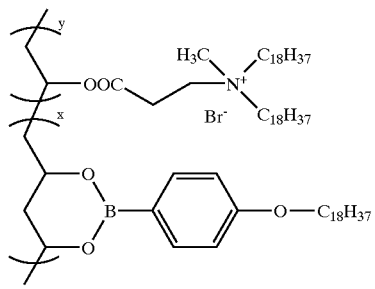

¹HNMR (δ ppm): 0.8–1.5(m, alkyl-CH₃, alkyl-CH₂), 2.2(m, OOC—CH₂), 3.3–3.5(m, N⁺—CH₃, N⁺—CH₂), 3.8–4.1 (m, phe-O—CH₂, COO—CH), 4.6(m, BO—CH), 6.9, 7.8(bs, phe-H)

| Compound No. | x | y | MW | Elemental analysis (C %, H %, N %) | |
|---|---|---|---|---|---|
| | | | | Found values | Calculated values |
| 49 | 0.9 | 0.1 | 500000 | 75.02, 10.88, 0.54 | 75.17, 10.79, 0.30 |
| 50 | 0.7 | 0.3 | 621000 | 73.59, 11.23, 1.10 | 73.77, 11.08, 0.80 |
| 51 | 0.5 | 0.5 | 764000 | 72.87, 11.53, 1.01 | 72.63, 11.32, 1.21 |

TABLE 13

Structure of boric diester compound

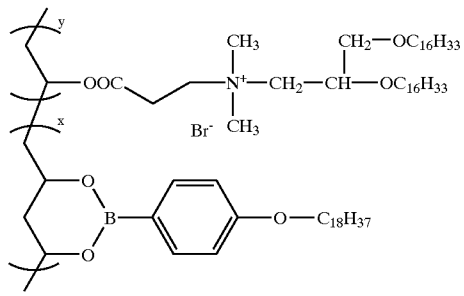

¹HNMR (δ ppm): 0.8–1.5(m, alkyl-CH₃, alkyl-CH₂), 2.2(t, OOC—CH₂), 3.3–3.5(m, alkyl-O—CH₂, alkyl-O—CH, N⁺—CH₃, N⁺—CH₂), 3.9(bs, phe-O—CH₂), 4.0

TABLE 13-continued (m, COO—CH), 4.6(m, BO—CH), 6.9, 7.8(bs, phe-H)

| Compound No. | x | y | MW | Elemental analysis (C %, H %, N %) | |
|---|---|---|---|---|---|
| | | | | Found values | Calculated values |
| 52 | 0.9 | 0.1 | 485000 | 74.39, 10.85, 0.57 | 74.66, 10.72, 0.30 |
| 53 | 0.7 | 0.3 | 619000 | 72.32, 10.96, 0.58 | 72.44, 10.88, 0.79 |
| 54 | 0.5 | 0.5 | 792000 | 70.47, 10.94, 1.35 | 70.68, 11.01, 1.18 |

TABLE 14

Structure of boric diester compound

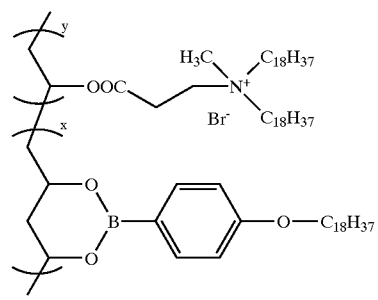

¹HNMR (δ ppm): 0.8–1.5(m, alkyl-CH₃, alkyl-CH₂), 3.6–4.0(m, N⁺—CH₃, N⁺—CH₂, phe-O—CH₂, COO—CH), 4.6 (m, BO—CH), 5.1(bs, OOC—CH₂—N⁺), 6.9, 7.8(bs, phe-H)

| Compound No. | x | y | MW | Elemental analysis (C %, H %, N %) | |
|---|---|---|---|---|---|
| | | | | Found values | Calculated values |
| 55 | 0.9 | 0.1 | 548000 | 74.89, 10.64, 0.57 | 75.14, 10.78, 0.30 |
| 56 | 0.7 | 0.3 | 609000 | 73.77, 11.31, 0.63 | 73.67, 11.06, 0.81 |
| 57 | 0.5 | 0.5 | 792000 | 72.46, 11.14, 1.07 | 72.47, 11.28, 1.22 |

TABLE 15

Structure of boric diester compound

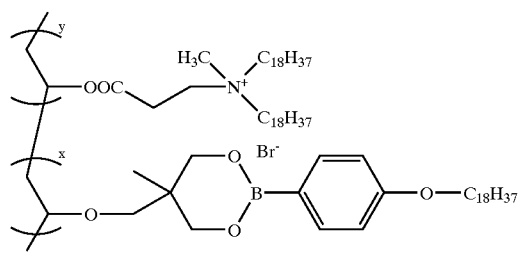

TABLE 15-continued

¹HNMR (δ ppm): 0.8–1.5(m, alkyl-CH₃, alkyl-CH₂), 2.2(bs, OOC—CH₂), 3.3–4.1(m, alkyl-O—CH₂, alkyl-O—CH, N⁺—CH₃, N⁺—CH₂, phe-O—CH₂), 4.0(m, COO—CH), 4.6(m, BO—CH₂), 6.9, 7.8(bs, phe-H)

| Compound | | | | Elemental analysis (C %, H %, N %) | |
|---|---|---|---|---|---|
| No. | x | y | MW | Found values | Calculated values |
| 58 | 0.9 | 0.1 | 564000 | 73.69, 10.58, 0.19 | 73.85, 10.75, 0.27 |
| 59 | 0.7 | 0.3 | 695000 | 73.12, 10.85, 0.70 | 72.92, 11.03, 0.74 |
| 60 | 0.5 | 0.5 | 858000 | 71.98, 11.53, 1.41 | 72.12, 11.27, 1.15 |

TABLE 16

Structure of boric diester compound

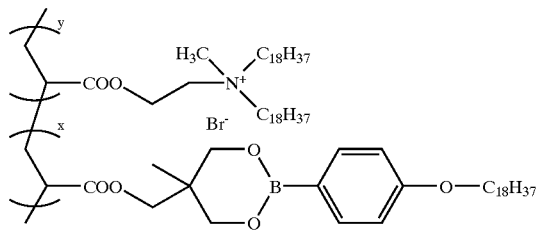

¹HNMR (δ ppm): 0.8–1.5(m, alkyl-CH₃, alkyl-CH₂), 2.2(m, OOC—CH), 3.3–4.0(m, N⁺—CH₃, N⁺—CH₂, phe-O—CH₂, COO—CH), 4.6(m, BO—CH₂), 6.9, 7.8(bs, phe-H)

| Compound | | | | Elemental analysis (C %, H %, N %) | |
|---|---|---|---|---|---|
| No. | x | y | MW | Found values | Calculated values |
| 61 | 0.9 | 0.1 | 188000 | 72.36, 10.51, 0.54 | 72.43, 10.25, 0.26 |
| 62 | 0.7 | 0.3 | 196000 | 72.14, 10.77, 1.00 | 71.92, 10.66, 0.72 |
| 63 | 0.5 | 0.5 | 210000 | 71.19, 10.83, 1.40 | 71.47, 11.02, 1.13 |

TABLE 17

Structure of boric diester compound

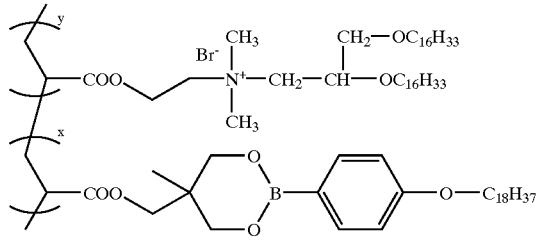

¹HNMR (δ ppm): 0.8–1.5(m, alkyl-CH₃, alkyl-CH₂), 2.2(m, OOC—CH), 3.3–4.1(m, alkyl-O—CH₂, alkyl-O—CH, N⁺—CH₃, N⁺—CH₂, phe-O—CH₂, COO—CH₂), 4.6(m, BO—CH₂), 6.9, 7.8(bs, phe-H)

| Compound | | | | Elemental analysis (C %, H %, N %) | |
|---|---|---|---|---|---|
| No. | x | y | MW | Found values | Calculated values |

TABLE 17-continued

| | | | | | |
|---|---|---|---|---|---|
| 64 | 0.9 | 0.1 | 182000 | 71.88, 10.20, 0.44 | 72.01, 10.19, 0.25 |
| 65 | 0.7 | 0.3 | 191000 | 70.53, 10.70, 0.83 | 70.75, 10.49, 0.71 |
| 66 | 0.5 | 0.5 | 208000 | 69.95, 10.50, 1.39 | 69.67, 10.74, 1.10 |

TABLE 18

Structure of boric diester compound

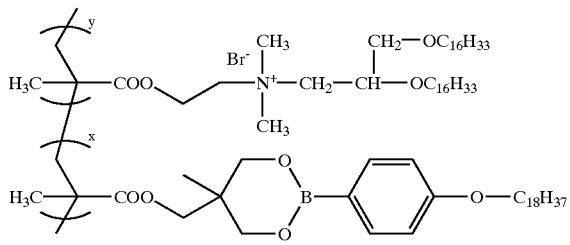

$^1$HNMR (δ ppm): 0.8–1.5(m, alkyl-CH$_3$, alkyl-CH$_2$), 3.3–4.1(m, alkyl-O—CH$_2$, alkyl-O—CH, N$^+$—CH$_3$, N$^+$—CH$_2$, phe-O—CH$_2$, COO—CH$_2$), 4.6(m, BO—CH$_2$), 6.9, 7.8(bs, phe-H)

| Compound No. | x | y | MW | Elemental analysis (C %, H %, N %) | |
|---|---|---|---|---|---|
| | | | | Found values | Calculated values |
| 67 | 0.9 | 0.1 | 712000 | 72.51, 10.00, 0.51 | 72.34, 10.29, 0.25 |
| 68 | 0.7 | 0.3 | 754000 | 71.29, 10.57, 0.81 | 71.10, 10.57, 0.69 |
| 69 | 0.5 | 0.5 | 832000 | 70.10, 10.61, 1.33 | 70.02, 10.82, 1.07 |

TABLE 19

Structure of boric diester compound

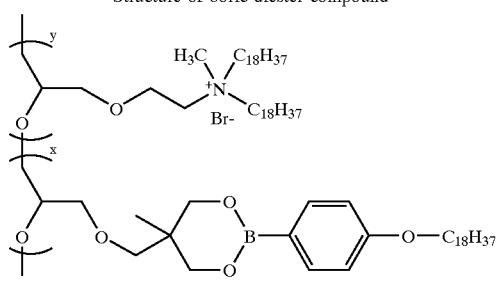

$^1$HNMR(δ ppm): 0.8–1.5(m, alkyl-CH$_3$, alkyl-CH$_2$), 3.3–3.9 (m, alkyl-O—CH$_2$, alkyl-O—CH, N$^+$—CH$_3$, N$^+$—CH$_2$, phe-O—CH$_2$), 4.6(m, BO—CH$_2$), 6.9, 7.8(bs, phe-H)

| Compound No. | x | y | MW | Elemental analysis (C %, H %, N %) | |
|---|---|---|---|---|---|
| | | | | Found values | Calculated values |
| 70 | 0.9 | 0.1 | 4180000 | 72.20, 10.41, 0.50 | 72.16, 10.58, 0.26 |
| 71 | 0.7 | 0.3 | 4440000 | 71.58, 11.23, 1.00 | 71.67, 10.96, 0.72 |
| 72 | 0.5 | 0.5 | 4720000 | 71.25, 11.41, 1.40 | 71.23, 11.30, 1.12 |

TABLE 20

Structure of boric diester compound

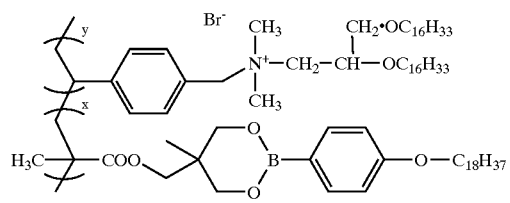

$^1$HNMR(δ ppm): 0.8–1.5(m, alkyl-CH$_3$, alkyl-CH$_2$), 2.6(m, phe-CH), 3.3–4.1(m, alkyl-O—CH$_2$, alkyl-O—CH, N$^+$—CH$_3$, N$^+$—CH$_2$, phe-O—CH$_2$, COO—CH$_2$), 4.6(m, phe-CH$_2$, BO—CH$_2$), 6.9, 7.8(bs, phe-H)

| Compound No. | x | y | MW | Elemental analysis (C %, H %, N %) | |
|---|---|---|---|---|---|
| | | | | Found values | Calculated values |
| 73 | 0.9 | 0.1 | 280000 | 72.80, 10.36, 0.31 | 72.93, 10.29, 0.25 |
| 74 | 0.7 | 0.3 | 356000 | 72.81, 10.72, 0.99 | 72.73, 10.55, 0.69 |
| 75 | 0.5 | 0.5 | 312000 | 72.51, 10.70, 1.37 | 72.56, 10.78, 1.07 |

TABLE 21

Structure of boric diester compound

[Chemical structure of boric diester compound with polymer backbone showing: CH₃, C₁₈H₃₇, N⁺, C₁₈H₃₇, COO, CH₃, B, OC₁₄H₂₉ groups]

¹HNMR(δ ppm): 0.8–1.5(m, alkyl-CH₃, alkyl-CH₂), 2.2–2.6 (m, OOC—CH, phe-CH), 3.3–3.5(m, N⁺—CH₃, N⁺—CH₂, alkyl-O—CH₂), 4.0(m, COO—CH₂), 4.6(m, BO—CH₂), 7.3, 7.8(bs, phe-H)

| Compound No. | x | y | MW | Elemental analysis (C %, H %, N %) | |
|---|---|---|---|---|---|
| | | | | Found values | Calculated values |
| 76 | 0.9 | 0.1 | 528000 | 74.59, 10.43, 0.30 | 74.88, 10.70, 0.31 |
| 77 | 0.7 | 0.3 | 650000 | 73.61, 11.26, 1.03 | 73.54, 11.02, 0.82 |
| 78 | 0.5 | 0.5 | 472000 | 72.38, 11.19, 1.50 | 72.47, 11.28, 1.22 |

TABLE 22

Structure of boric diester compound

[Chemical structure of boric diester compound with polymer backbone showing: CH₃, C₁₈H₃₇, N⁺, C₁₈H₃₇, Br⁻, CH₃, B, OC₁₄H₂₉ groups]

¹HNMR(δ ppm): 0.8–1.5(m, alkyl-CH₃, alkyl-CH₂), 2.6(m, phe-CH), 3.3–3.5(m, N⁺—CH₃, N⁺—CH₂, alkyl-O—CH₂, N—CH₂-phe), 4.6(m, BO—CH₂), 7.0–7.6(bs, phe-H)

| Compound No. | x | y | MW | Elemental analysis (C %, H %, N %) | |
|---|---|---|---|---|---|
| | | | | Found values | Calculated values |
| 79 | 0.9 | 0.1 | 419000 | 75.33, 10.84, 0.61 | 75.63, 10.70, 0.31 |
| 80 | 0.7 | 0.3 | 360000 | 75.32, 10.89, 1.10 | 75.55, 11.02, 0.81 |
| 81 | 0.5 | 0.5 | 527000 | 75.37, 11.46, 1.21 | 75.48, 11.28, 1.21 |

TABLE 23

| Abbreviation | Structure of fat-soluble anion salt |
|---|---|
| TFPB | [Structure: tetrakis(3,5-bis(trifluoromethyl)phenyl)borate sodium salt, Na⁺] |
| TCPB | [Structure: tetrakis(4-chlorophenyl)borate potassium salt, K⁺] |
| DESS | Na⁺ SO₃⁻—CH(COO—CH₂—CH(C₂H₅)C₄H₉)—COO—CH₂—CH(C₂H₅)C₄H₉ |

The amounts of boric diester compound or onium salt compound used in these examples are expressed in terms of parts by weight of the boric diester compound or the onium salt compound per 100 parts by weight of the combined amount of the boric diester compound and the onium salt compound. Where a polymer is added to these compounds, they are expressed in terms of parts by weight of the boric diester compound or the onium salt compound per 100 parts by weight of the combined amount of the boric diester compound, the onium salt compound and the polymer. The amount of fat-soluble anion salt used is expressed as its molar ratio based on the onium salt compound [i.e., (the number of moles of the fat-soluble anion salt)/(the number of moles of the onium salt compound)].

In these examples, the term "slope" refers to the value of s in the following equation (Nernst equation), and indicates the change in membrane potential (mV) which occurs when the concentration of the ionic species to be determined (i.e., hydrogencarbonate ion) is altered from $10^{-3}$ M to $10^{-2}$ M.

$$E_i = E_i^0 - s \log(a_i)$$

wherein $E_i^0$ is the electric potential observed when a molecular species (i) having an activity $a_i$ is absent, $E_i$ is the electric potential observed when the molecular species (i) having an activity $a_i$ is present, and s is the slope.

The hydrogencarbonate ion selectivity coefficients ($K_{HCO_3,X}$) relative to various ions were determined according to the following equation.

$$\log K_{HCO_3,X} = \frac{E_X - E_{HCO_3}}{-s}$$

wherein $K_{HCO_3,X}$ is the hydrogencarbonate ion selectivity coefficient relative to an ion X, $E_X$ is the electric potential for the interfering ionic species, $E_{HCO_3}$ is the electric potential for hydrogencarbonate ion, and s is the slope.

The following preparation examples are concerned with the preparation of several typical ones of the onium salt compounds and aromatic boric diesters listed in the foregoing Tables 1 to 22. Other compounds than those described in the preparation examples may be synthesized in substantially the same manner as in the preparation examples.

Preparation Example 1
(Compound No. 36)

2.99 g (10.4 mmol) of 4-(2-ethylhexyloxy)bromobenzene was suspended in 50 ml of tetrahydrofuran. After this suspension was cooled to −70° C., a solution of n-butyllithium (20.9 mmol) in hexane was slowly added dropwise thereto. After the reaction mixture was stirred at −70° C. for 30 minutes, 21.7 g (209 mmol) of trimethoxyborane was slowly added dropwise thereto. After the stirring was continued at −70° C. for 1 hour, the reaction mixture was slowly heated to ordinary temperature and then stirred at ordinary temperature for 2 hours. Moreover, after hydrochloric acid was added to the reaction mixture so as to adjust its pH to a value of 1 or less, and the reaction mixture was stirred at ordinary temperature for 20 hours, water and ether were added thereto and the organic layer was separated. The solvent was evaporated under reduced pressure to obtain 3 g of a pale-yellow oily material.

3 g of the resulting pale-yellow oily material was dissolved in 100 ml of toluene, and this solution was mixed with 30 ml of an aqueous solution containing 1 g of polyvinyl alcohol (with a degree of polymerization of 2,000). Using a Dean-Stark trap, this mixture was heated under reflux so that the water contained in the system might be removed by azeotropic distillation. After completion of the reaction, the toluene was evaporated under reduced pressure. The residue was passed through a silica gel column (with chloroform) to obtain 1.2 g of a white solid. When the purified product was subjected to $^1$HNMR spectroscopy [in $CDCl_3$ by using TMS as a standard (0.00 ppm)], the following results were obtained.

$^1$HNMR: 7.7 ppm (bs; 2H, Phe-H), 6.9 ppm (bs; 2H, Phe-H), 4.6–4.7 ppm (m; 2H, —O—CH<), 3.8 ppm (bs; 2H, Phe-O—$CH_2$), 2.5–0.7 (m; 19H, CH, $CH_2$, $CH_3$)

IR (KBr method): 1376 $cm^{-1}$ (B-O stretching vibrations).

Average molecular weight determined by gel permeation chromatography: 330,000.

Preparation Example 2
(Compound No. 39)

In the same manner as in Preparation Example 1, a pale-yellow oily material was obtained by reacting 4-(octadecyloxy)bromobenzene with trimethoxyborane in the presence of n-butyllithium. Then, a boric diester compound was synthesized from the above pale-yellow oily material and polyvinyl alcohol in the same manner as in Preparation Example 1. When the purified product was subjected to $^1$HNMR spectroscopy [in $CDCl_3$ by using TMS as a standard (0.00 ppm)], the following results were obtained.

$^1$HNMR: 7.7 ppm (bs; 2H, Phe-H), 6.9 ppm (bs; 2H, Phe-H), 4.6–4.7 ppm (m; 2H, —O—CH<), 3.8 ppm (bs; 2H, Phe-O—$CH_2$), 2.5–0.7 (m; 39H, CH, $CH_2$, $CH_3$)

IR (KBr method): 1376 $cm^{-1}$ (B-O stretching vibrations).

Average molecular weight determined by gel permeation chromatography: 534,000.

Example 1
(Formation of Membrane Nos. 1–174)

The onium salt compounds, boric diester compounds and optional polymers shown in Tables 24–31 were used in the respective amounts indicated in Tables 24–31. For each Membrane No., these ingredients were dissolved in 2.5 ml of tetrahydrofuran, and the resulting solution was cast in a Petri dish made of glass and having a diameter of 27 mm. A membranous material was obtained by evaporating the solvent at 20° C. under atmospheric pressure for 24 hours and then drying the residue in a vacuum of 1 mmHg for 5 hours. The state of dispersion in the membranes thus obtained is also shown in Tables 24–31.

TABLE 24

| Membrane No. | Onium salt compound | | | Boric diester compound | | | Polymer | | State of dispersion in membrane | Slope (mV/dec) | Selectivity coefficients relative to anions | | |
|---|---|---|---|---|---|---|---|---|---|---|---|---|---|
| | Compound No. | Weight (mg) | Compositional ratio (pbw*) | Compound No. | Weight (mg) | Compositional ratio (pbw*) | Designation | Weight (mg) | | | $NO_3^-$ | $Cl^-$ | $SaI^-$ |
| Present invention | | | | | | | | | | | | | |
| 1 | 1 | 0.16 | 0.11 | 23 | 100.0 | 66.0 | PVC | 50.0 | Uniformly dispersed | 50.2 | 0.07 | 0.01 | 0.55 |
| 2 | 1 | 8.1 | 5.12 | 23 | 100.0 | 63.3 | PVC | 50.0 | Uniformly dispersed | 58.3 | 0.03 | 0.01 | 0.67 |
| 3 | 1 | 40.5 | 21.3 | 23 | 100.0 | 52.5 | PVC | 50.0 | Uniformly dispersed | 43.5 | 0.12 | 0.07 | 0.63 |
| 4 | 2 | 22.2 | 12.9 | 23 | 100.0 | 58.1 | PVC | 50.0 | Uniformly dispersed | 47.9 | 0.05 | 0.03 | 0.43 |
| 5 | 2 | 22.2 | 12.9 | 23 | 100.0 | 58.1 | PVdC | 50.0 | Uniformly dispersed | 50.9 | 0.05 | 0.02 | 0.43 |
| 6 | 2 | 2.2 | 1.73 | 23 | 100.0 | 78.6 | PVdC | 25.0 | Uniformly dispersed | 45.8 | 0.07 | 0.01 | 0.55 |
| 7 | 3 | 22.2 | 12.9 | 23 | 100.0 | 57.8 | PVC | 50.0 | Uniformly dispersed | 51.3 | 0.07 | 0.03 | 0.53 |
| 8 | 4 | 0.16 | 0.11 | 23 | 100.0 | 66.6 | PVC | 50.0 | Uniformly dispersed | 46.5 | 0.06 | 0.02 | 0.40 |
| 9 | 4 | 8.0 | 5.06 | 23 | 100.0 | 63.3 | PVC | 50.0 | Uniformly dispersed | 46.6 | 0.06 | 0.02 | 0.52 |
| 10 | 4 | 32.0 | 17.6 | 23 | 100.0 | 54.9 | PVC | 50.0 | Uniformly dispersed | 46.6 | 0.13 | 0.06 | 0.73 |
| 11 | 5 | 11.7 | 7.23 | 23 | 100.0 | 62.0 | PVC | 50.0 | Uniformly dispersed | 51.2 | 0.05 | 0.02 | 0.61 |
| 12 | 6 | 14.0 | 8.53 | 23 | 100.0 | 61.0 | PVC | 50.0 | Uniformly dispersed | 50.5 | 0.04 | 0.02 | 0.77 |
| 13 | 7 | 17.8 | 10.6 | 23 | 100.0 | 59.6 | PVC | 50.0 | Uniformly dispersed | 49.5 | 0.05 | 0.02 | 0.67 |
| 14 | 8 | 0.73 | 0.48 | 23 | 100.0 | 66.3 | PVC | 50.0 | Uniformly dispersed | 46.8 | 0.05 | 0.01 | 0.72 |
| 15 | 8 | 7.3 | 4.64 | 23 | 100.0 | 63.6 | PVC | 50.0 | Uniformly dispersed | 53.5 | 0.07 | 0.02 | 0.73 |
| 16 | 8 | 36.5 | 19.6 | 23 | 100.0 | 53.6 | PVC | 50.0 | Uniformly dispersed | 55.5 | 0.10 | 0.02 | 0.63 |
| 17 | 9 | 19.2 | 11.3 | 23 | 100.0 | 59.1 | PVC | 50.0 | Uniformly dispersed | 55.2 | 0.06 | 0.01 | 0.46 |
| 18 | 10 | 50.0 | 33.3 | 23 | 100.0 | 66.7 | — | — | Uniformly dispersed | 49.9 | 0.06 | 0.01 | 0.52 |
| 19 | 10 | 75.0 | 50.0 | 23 | 75.0 | 50.0 | — | — | Uniformly dispersed | 53.3 | 0.06 | 0.01 | 0.48 |
| 20 | 10 | 100.0 | 66.7 | 23 | 50.0 | 33.3 | — | — | Uniformly dispersed | 57.7 | 0.07 | 0.03 | 0.48 |
| 21 | 11 | 50.0 | 33.3 | 23 | 100.0 | 66.7 | — | — | Uniformly dispersed | 46.9 | 0.05 | 0.01 | 0.50 |
| 22 | 12 | 100.0 | 66.7 | 23 | 50.0 | 33.3 | — | — | Uniformly dispersed | 48.3 | 0.07 | 0.02 | 0.49 |

TABLE 24-continued

| Membrane No. | Onium salt compound | | | Boric diester compound | | | Polymer | | State of dispersion in membrane | Slope (mV/dec) | Selectivity coefficients relative to anions | | |
|---|---|---|---|---|---|---|---|---|---|---|---|---|---|
| | Compound No. | Weight (mg) | Compositional ratio (pbw*) | Compound No. | Weight (mg) | Compositional ratio (pbw*) | Designation | Weight (mg) | | | $NO_3^-$ | $Cl^-$ | $SaI^-$ |

*pbw = part by weight

TABLE 25

| Membrane No. | Onium salt compound | | | Boric diester compound | | | Polymer | | State of dispersion in membrane | Slope (mV/dec) | Selectivity coefficients relative to anions | | |
|---|---|---|---|---|---|---|---|---|---|---|---|---|---|
| | Compound No. | Weight (mg) | Compositional ratio (pbw*) | Compound No. | Weight (mg) | Compositional ratio (pbw*) | Designation | Weight (mg) | | | $NO_3^-$ | $Cl^-$ | $SaI^-$ |
| Present invention | | | | | | | | | | | | | |
| 23 | 12 | 115.0 | 76.7 | 23 | 35.0 | 23.3 | — | — | Uniformly dispersed | 46.5 | 0.06 | 0.01 | 0.58 |
| 24 | 12 | 125.0 | 71.8 | 23 | 49.0 | 28.2 | — | — | Uniformly dispersed | 51.4 | 0.04 | 0.01 | 0.41 |
| 25 | 13 | 50.0 | 33.3 | 23 | 100.0 | 66.7 | — | — | Uniformly dispersed | 55.5 | 0.04 | 0.03 | 0.43 |
| 26 | 1 | 8.1 | 5.12 | 24 | 100.0 | 63.3 | PVC | 50.0 | Uniformly dispersed | 49.5 | 0.04 | 0.01 | 0.64 |
| 27 | 1 | 8.1 | 5.12 | 25 | 100.0 | 63.3 | PVC | 50.0 | Uniformly dispersed | 48.2 | 0.06 | 0.01 | 0.50 |
| 28 | 1 | 8.1 | 5.12 | 26 | 100.0 | 63.3 | PVdC | 50.0 | Uniformly dispersed | 51.3 | 0.05 | 0.03 | 0.58 |
| 29 | 1 | 8.1 | 5.12 | 27 | 100.0 | 63.3 | PVdC | 50.0 | Uniformly dispersed | 53.8 | 0.05 | 0.02 | 0.75 |
| 30 | 1 | 8.1 | 5.12 | 28 | 100.0 | 63.3 | PVdC | 50.0 | Uniformly dispersed | 48.9 | 0.06 | 0.03 | 0.56 |
| 31 | 1 | 8.1 | 5.12 | 29 | 100.0 | 63.3 | PVdC | 50.0 | Uniformly dispersed | 44.7 | 0.06 | 0.03 | 0.66 |
| 32 | 1 | 8.1 | 5.12 | 34 | 150.0 | 63.3 | — | — | Uniformly dispersed | 46.7 | 0.07 | 0.03 | 0.63 |
| 33 | 1 | 8.1 | 5.12 | 35 | 150.0 | 63.3 | — | — | Uniformly dispersed | 45.1 | 0.05 | 0.01 | 0.47 |
| 34 | 2 | 11.0 | 6.83 | 25 | 100.0 | 62.1 | PVdC | 50.0 | Uniformly dispersed | 51.0 | 0.04 | 0.01 | 0.54 |
| 35 | 3 | 22.2 | 12.9 | 28 | 100.0 | 58.1 | PVdC | 50.0 | Uniformly dispersed | 52.4 | 0.05 | 0.01 | 0.69 |
| 36 | 4 | 16.0 | 9.64 | 26 | 100.0 | 60.2 | PVdC | 50.0 | Uniformly dispersed | 49.0 | 0.07 | 0.02 | 0.63 |
| 37 | 4 | 16.0 | 9.64 | 28 | 100.0 | 60.2 | PVdC | 50.0 | Uniformly dispersed | 54.0 | 0.07 | 0.03 | 0.52 |
| 38 | 4 | 16.0 | 9.64 | 35 | 150.0 | 60.2 | — | — | Uniformly dispersed | 51.4 | 0.06 | 0.01 | 0.73 |
| 39 | 5 | 11.7 | 7.23 | 27 | 100.0 | 61.8 | PVdC | 50.0 | Uniformly dispersed | 51.6 | 0.05 | 0.03 | 0.63 |
| 40 | 6 | 14.0 | 8.53 | 27 | 100.0 | 61.0 | PVdC | 50.0 | Uniformly dispersed | 45.3 | 0.06 | 0.03 | 0.59 |
| 41 | 7 | 17.9 | 10.7 | 29 | 100.0 | 59.6 | PVdC | 50.0 | Uniformly dispersed | 43.9 | 0.04 | 0.01 | 0.59 |
| 42 | 8 | 0.7 | 0.46 | 24 | 100.0 | 66.4 | PVC | 50.0 | Uniformly dispersed | 51.6 | 0.04 | 0.03 | 0.71 |
| 43 | 8 | 7.3 | 4.64 | 25 | 100.0 | 63.6 | PVC | 50.0 | Uniformly dispersed | 54.7 | 0.05 | 0.03 | 0.61 |
| 44 | 8 | 16.6 | 10.0 | 28 | 100.0 | 60.0 | PVC | 50.0 | Uniformly dispersed | 46.2 | 0.05 | 0.01 | 0.50 |
| 45 | 8 | 33.5 | 19.9 | 29 | 84.5 | 50.3 | PVdC | 50.0 | Uniformly dispersed | 49.8 | 0.05 | 0.01 | 0.57 |
| 46 | 8 | 7.3 | 4.64 | 34 | 150.0 | 95.3 | — | — | Uniformly dispersed | 56.3 | 0.18 | 0.07 | 0.65 |

*pbw = part by weight

TABLE 26

| Membrane No. | Onium salt compound | | | Boric diester compound | | | Polymer | | State of dispersion in membrane | Slope (mV/dec) | Selectivity coefficients relative to anions | | |
|---|---|---|---|---|---|---|---|---|---|---|---|---|---|
| | Compound No. | Weight (mg) | Compositional ratio (pbw*) | Compound No. | Weight (mg) | Compositional ratio (pbw*) | Designation | Weight (mg) | | | $NO_3^-$ | $Cl^-$ | $SaI^-$ |
| Present invention | | | | | | | | | | | | | |
| 47 | 9 | 19.2 | 5.44 | 27 | 100.0 | 59.1 | PVC | 50.0 | Uniformly dispersed | 51.2 | 0.06 | 0.02 | 0.58 |
| 48 | 10 | 10.2 | 9.26 | 25 | 100.0 | 90.7 | — | — | Uniformly dispersed | 52.2 | 0.15 | 0.08 | 0.61 |
| 49 | 10 | 20.3 | 14.0 | 35 | 125.0 | 86.0 | — | — | Uniformly dispersed | 48.3 | 0.14 | 0.07 | 0.71 |
| 50 | 11 | 49.1 | 32.9 | 27 | 100.0 | 67.1 | — | — | Uniformly dispersed | 46.9 | 0.05 | 0.01 | 0.53 |
| 51 | 11 | 18.3 | 11.6 | 35 | 140.0 | 81.7 | — | — | Uniformly dispersed | 53.6 | 0.17 | 0.06 | 0.82 |
| 52 | 12 | 75.0 | 42.9 | 24 | 100.0 | 57.1 | — | — | Uniformly dispersed | 51.7 | 0.04 | 0.01 | 0.67 |
| 53 | 12 | 75.0 | 42.9 | 26 | 100.0 | 57.1 | — | — | Uniformly dispersed | 47.4 | 0.06 | 0.03 | 0.66 |
| 54 | 12 | 75.0 | 42.9 | 28 | 100.0 | 57.1 | — | — | Uniformly dispersed | 45.8 | 0.06 | 0.02 | 0.48 |
| 55 | 12 | 75.0 | 42.9 | 29 | 100.0 | 57.1 | — | — | Uniformly dispersed | 44.4 | 0.05 | 0.03 | 0.70 |

TABLE 26-continued

| | Onium salt compound | | | Boric diester compound | | | Polymer | | | | Selectivity coefficients relative to anions | | |
|---|---|---|---|---|---|---|---|---|---|---|---|---|---|
| Membrane No. | Compound No. | Weight (mg) | Compositional ratio (pbw*) | Compound No. | Weight (mg) | Compositional ratio (pbw*) | Designation | Weight (mg) | State of dispersion in membrane | Slope (mV/dec) | $NO_3^-$ | $Cl^-$ | $SaI^-$ |
| 56 | 12 | 75.0 | 42.9 | 34 | 100.0 | 57.1 | — | — | Uniformly dispersed | 47.4 | 0.06 | 0.02 | 0.69 |
| 57 | 13 | 75.0 | 42.9 | 24 | 100.0 | 57.1 | — | — | Uniformly dispersed | 46.5 | 0.04 | 0.01 | 0.50 |
| 58 | 13 | 75.0 | 42.9 | 28 | 100.0 | 57.1 | — | — | Uniformly dispersed | 57.1 | 0.05 | 0.03 | 0.53 |
| 59 | 13 | 75.0 | 42.9 | 34 | 100.0 | 57.1 | — | — | Uniformly dispersed | 53.7 | 0.05 | 0.03 | 0.49 |
| 60 | 13 | 75.0 | 42.9 | 35 | 100.0 | 57.1 | — | — | Uniformly dispersed | 56.6 | 0.05 | 0.02 | 0.57 |
| 61 | 14 | 10.5 | 6.5 | 23 | 100.0 | 62.3 | PVC | 50.0 | Uniformly dispersed | 51.3 | 0.07 | 0.02 | 0.78 |
| 62 | 14 | 31.3 | 17.3 | 23 | 100.0 | 55.2 | PVC | 50.0 | Uniformly dispersed | 49.5 | 0.07 | 0.01 | 0.86 |
| 63 | 15 | 5.3 | 3.4 | 23 | 100.0 | 64.4 | PVC | 50.0 | Uniformly dispersed | 56.0 | 0.06 | 0.03 | 0.46 |
| 64 | 15 | 43.2 | 22.4 | 23 | 100.0 | 51.8 | PVC | 50.0 | Uniformly dispersed | 52.0 | 0.09 | 0.01 | 0.59 |
| 65 | 16 | 0.10 | 0.07 | 23 | 100.0 | 66.6 | PVC | 50.0 | Uniformly dispersed | 50.5 | 0.04 | 0.01 | 0.81 |
| 66 | 16 | 28.6 | 16.0 | 23 | 100.0 | 56.0 | PVC | 50.0 | Uniformly dispersed | 47.1 | 0.05 | 0.02 | 0.59 |
| 67 | 17 | 10.3 | 6.4 | 23 | 100.0 | 62.4 | PVC | 50.0 | Uniformly dispersed | 47.1 | 0.08 | 0.02 | 0.61 |
| 68 | 17 | 25.5 | 14.5 | 23 | 100.0 | 57.0 | PVC | 50.0 | Uniformly dispersed | 54.4 | 0.06 | 0.01 | 0.74 |
| 69 | 18 | 1.36 | 0.90 | 23 | 100.0 | 66.1 | PVC | 50.0 | Uniformly dispersed | 56.9 | 0.07 | 0.02 | 0.77 |

*pbw = part by weight

TABLE 27

| | Onium salt compound | | | Boric diester compound | | | Polymer | | | | Selectivity coefficients relative to anions | | |
|---|---|---|---|---|---|---|---|---|---|---|---|---|---|
| Membrane No. | Compound No. | Weight (mg) | Compositional ratio (pbw*) | Compound No. | Weight (mg) | Compositional ratio (pbw*) | Designation | Weight (mg) | State of dispersion in membrane | Slope (mV/dec) | $NO_3^-$ | $Cl^-$ | $SaI^-$ |
| Present invention | | | | | | | | | | | | | |
| 70 | 18 | 22.8 | 13.2 | 23 | 100.0 | 57.9 | PVC | 50.0 | Uniformly dispersed | 54.1 | 0.06 | 0.01 | 0.67 |
| 71 | 19 | 1.50 | 0.99 | 23 | 100.0 | 66.0 | PVC | 50.0 | Uniformly dispersed | 50.0 | 0.07 | 0.02 | 0.71 |
| 72 | 19 | 8.35 | 5.3 | 23 | 100.0 | 63.2 | PVC | 50.0 | Uniformly dispersed | 49.3 | 0.05 | 0.01 | 0.64 |
| 73 | 20 | 3.68 | 2.4 | 23 | 100.0 | 65.1 | PVC | 50.0 | Uniformly dispersed | 54.2 | 0.06 | 0.01 | 0.72 |
| 74 | 20 | 20.4 | 12.0 | 23 | 100.0 | 58.7 | PVC | 50.0 | Uniformly dispersed | 55.5 | 0.06 | 0.02 | 0.80 |
| 75 | 21 | 25.9 | 14.7 | 23 | 100.0 | 56.9 | PVC | 50.0 | Uniformly dispersed | 47.6 | 0.07 | 0.01 | 0.60 |
| 76 | 21 | 57.3 | 27.6 | 23 | 100.0 | 48.2 | PVC | 50.0 | Uniformly dispersed | 58.0 | 0.05 | 0.02 | 0.73 |
| 77 | 22 | 21.7 | 12.6 | 23 | 100.0 | 58.2 | PVC | 50.0 | Uniformly dispersed | 49.3 | 0.08 | 0.02 | 0.74 |
| 78 | 22 | 65.4 | 30.4 | 23 | 100.0 | 46.4 | PVC | 50.0 | Uniformly dispersed | 51.2 | 0.07 | 0.01 | 0.59 |
| 79 | 14 | 46.5 | 23.7 | 24 | 100.0 | 50.9 | PVC | 50.0 | Uniformly dispersed | 46.5 | 0.08 | 0.03 | 0.81 |
| 80 | 15 | 13.2 | 8.1 | 24 | 100.0 | 61.3 | PVC | 50.0 | Uniformly dispersed | 54.4 | 0.05 | 0.02 | 0.67 |
| 81 | 16 | 10.5 | 6.5 | 25 | 100.0 | 62.3 | PVC | 50.0 | Uniformly dispersed | 54.6 | 0.04 | 0.01 | 0.62 |
| 82 | 17 | 10.5 | 6.5 | 25 | 100.0 | 62.3 | PVC | 50.0 | Uniformly dispersed | 49.9 | 0.08 | 0.01 | 0.64 |
| 83 | 18 | 10.5 | 6.5 | 26 | 100.0 | 62.3 | PVC | 50.0 | Uniformly dispersed | 57.2 | 0.07 | 0.02 | 0.75 |
| 84 | 19 | 10.5 | 6.5 | 26 | 100.0 | 62.3 | PVC | 50.0 | Uniformly dispersed | 48.8 | 0.06 | 0.01 | 0.81 |
| 85 | 20 | 10.5 | 6.5 | 27 | 100.0 | 62.3 | PVC | 50.0 | Uniformly dispersed | 52.3 | 0.06 | 0.01 | 0.87 |
| 86 | 21 | 45.0 | 23.1 | 27 | 100.0 | 51.3 | PVC | 50.0 | Uniformly dispersed | 52.0 | 0.07 | 0.01 | 0.84 |
| 87 | 22 | 45.0 | 23.1 | 28 | 100.0 | 51.3 | PVC | 50.0 | Uniformly dispersed | 51.1 | 0.04 | 0.02 | 0.64 |
| 88 | 14 | 46.5 | 23.7 | 28 | 100.0 | 50.9 | PVC | 50.0 | Uniformly dispersed | 56.3 | 0.09 | 0.02 | 0.62 |
| 89 | 15 | 13.2 | 8.1 | 29 | 100.0 | 61.3 | PVC | 50.0 | Uniformly dispersed | 49.5 | 0.05 | 0.01 | 0.71 |
| 90 | 16 | 10.5 | 6.5 | 29 | 100.0 | 62.3 | PVC | 50.0 | Uniformly dispersed | 52.2 | 0.06 | 0.01 | 0.76 |
| 91 | 17 | 10.5 | 6.5 | 30 | 100.0 | 62.3 | PVC | 50.0 | Uniformly dispersed | 54.6 | 0.06 | 0.01 | 0.58 |
| 92 | 18 | 10.5 | 6.5 | 30 | 100.0 | 62.3 | PVC | 50.0 | Uniformly dispersed | 47.6 | 0.07 | 0.01 | 0.57 |
| 93 | 19 | 10.5 | 6.5 | 31 | 100.0 | 62.3 | PVC | 50.0 | Uniformly dispersed | 53.3 | 0.04 | 0.01 | 0.62 |

*pbw = part by weight

TABLE 28

| Membrane No. | Onium salt compound Compound No. | Weight (mg) | Compositional ratio (pbw*) | Boric diester compound Compound No. | Weight (mg) | Compositional ratio (pbw*) | Polymer Designation | Weight (mg) | State of dispersion in membrane | Slope (mV/dec) | Selectivity coefficients relative to anions NO$_3^-$ | Cl$^-$ | SaI$^-$ |
|---|---|---|---|---|---|---|---|---|---|---|---|---|---|
| Present invention | | | | | | | | | | | | | |
| 94 | 20 | 10.5 | 6.5 | 31 | 100.0 | 62.3 | PVC | 50.0 | Uniformly dispersed | 54.1 | 0.06 | 0.01 | 0.67 |
| 95 | 21 | 35.0 | 18.9 | 32 | 100.0 | 54.1 | PVC | 50.0 | Uniformly dispersed | 47.9 | 0.07 | 0.01 | 0.70 |
| 96 | 22 | 35.0 | 18.9 | 32 | 100.0 | 54.1 | PVC | 50.0 | Uniformly dispersed | 55.5 | 0.06 | 0.02 | 0.65 |
| 97 | 14 | 45.0 | 23.1 | 33 | 100.0 | 51.3 | PVC | 50.0 | Uniformly dispersed | 56.2 | 0.07 | 0.02 | 0.81 |
| 98 | 15 | 45.0 | 23.1 | 33 | 100.0 | 51.3 | PVC | 50.0 | Uniformly dispersed | 52.0 | 0.06 | 0.01 | 0.74 |
| 99 | 1 | 8.1 | 7.5 | 36 | 100.0 | 92.5 | — | — | Uniformly dispersed | 57.3 | 0.05 | 0.01 | 0.65 |
| 100 | 1 | 32.4 | 24.5 | 36 | 100.0 | 75.5 | — | — | Uniformly dispersed | 48.9 | 0.06 | 0.01 | 0.69 |
| 101 | 3 | 22.2 | 18.2 | 36 | 100.0 | 81.8 | — | — | Uniformly dispersed | 46.6 | 0.05 | 0.02 | 0.63 |
| 102 | 3 | 44.4 | 30.7 | 36 | 100.0 | 69.3 | — | — | Uniformly dispersed | 54.1 | 0.05 | 0.01 | 0.78 |
| 103 | 11 | 18.3 | 15.5 | 36 | 100.0 | 84.5 | — | — | Uniformly dispersed | 54.7 | 0.06 | 0.01 | 0.84 |
| 104 | 11 | 50.0 | 33.3 | 36 | 100.0 | 66.7 | — | — | Uniformly dispersed | 49.9 | 0.06 | 0.01 | 0.64 |
| 105 | 12 | 50.0 | 33.3 | 36 | 100.0 | 66.7 | — | — | Uniformly dispersed | 56.9 | 0.05 | 0.02 | 0.79 |
| 106 | 12 | 80.0 | 44.4 | 36 | 100.0 | 55.6 | — | — | Uniformly dispersed | 55.2 | 0.05 | 0.01 | 0.61 |
| 107 | 14 | 50.0 | 33.3 | 36 | 100.0 | 66.7 | — | — | Uniformly dispersed | 54.6 | 0.07 | 0.01 | 0.77 |
| 108 | 14 | 80.0 | 44.4 | 36 | 100.0 | 55.6 | — | — | Uniformly dispersed | 49.7 | 0.06 | 0.01 | 0.77 |
| 109 | 15 | 50.0 | 33.3 | 36 | 100.0 | 66.7 | — | — | Uniformly dispersed | 44.4 | 0.06 | 0.02 | 0.65 |
| 110 | 15 | 80.0 | 44.4 | 36 | 100.0 | 55.6 | — | — | Uniformly dispersed | 52.1 | 0.06 | 0.01 | 0.64 |
| 111 | 5 | 11.7 | 10.5 | 37 | 100.0 | 89.5 | — | — | Uniformly dispersed | 49.7 | 0.07 | 0.02 | 0.85 |
| 112 | 7 | 17.9 | 15.2 | 37 | 100.0 | 84.8 | — | — | Uniformly dispersed | 56.3 | 0.05 | 0.02 | 0.70 |
| 113 | 8 | 0.7 | 0.7 | 38 | 100.0 | 99.3 | — | — | Uniformly dispersed | 51.0 | 0.05 | 0.01 | 0.63 |
| 114 | 10 | 10.2 | 9.3 | 38 | 100.0 | 90.7 | — | — | Uniformly dispersed | 57.4 | 0.07 | 0.01 | 0.70 |
| 115 | 1 | 8.1 | 7.5 | 39 | 100.0 | 92.5 | — | — | Uniformly dispersed | 45.9 | 0.07 | 0.01 | 0.80 |
| 116 | 1 | 24.3 | 19.5 | 39 | 100.0 | 80.5 | — | — | Uniformly dispersed | 54.5 | 0.06 | 0.01 | 0.75 |

*pbw = part by weight

TABLE 29

| Membrane No. | Onium salt compound Compound No. | Weight (mg) | Compositional ratio (pbw*) | Boric diester compound Compound No. | Weight (mg) | Compositional ratio (pbw*) | Polymer Designation | Weight (mg) | State of dispersion in membrane | Slope (mV/dec) | Selectivity coefficients relative to anions NO$_3^-$ | Cl$^-$ | SaI$^-$ |
|---|---|---|---|---|---|---|---|---|---|---|---|---|---|
| Present invention | | | | | | | | | | | | | |
| 117 | 5 | 11.7 | 10.5 | 39 | 100.0 | 89.5 | — | — | Uniformly dispersed | 52.3 | 0.06 | 0.01 | 0.64 |
| 118 | 5 | 33.5 | 25.1 | 39 | 100.0 | 74.9 | — | — | Uniformly dispersed | 54.4 | 0.06 | 0.01 | 0.68 |
| 119 | 8 | 7.3 | 6.8 | 39 | 100.0 | 93.2 | — | — | Uniformly dispersed | 49.8 | 0.05 | 0.02 | 0.67 |
| 120 | 8 | 33.5 | 25.1 | 39 | 100.0 | 74.9 | — | — | Uniformly dispersed | 56.0 | 0.07 | 0.01 | 0.72 |
| 121 | 9 | 19.2 | 16.1 | 39 | 100.0 | 83.9 | — | — | Uniformly dispersed | 54.1 | 0.06 | 0.01 | 0.74 |
| 122 | 9 | 35.0 | 25.9 | 39 | 100.0 | 74.1 | — | — | Uniformly dispersed | 55.7 | 0.06 | 0.01 | 0.68 |
| 123 | 11 | 18.3 | 15.5 | 39 | 100.0 | 84.5 | — | — | Uniformly dispersed | 58.0 | 0.06 | 0.02 | 0.78 |
| 124 | 11 | 50.0 | 33.3 | 39 | 100.0 | 66.7 | — | — | Uniformly dispersed | 49.7 | 0.07 | 0.01 | 0.65 |
| 125 | 12 | 30.0 | 23.1 | 39 | 100.0 | 76.9 | — | — | Uniformly dispersed | 49.7 | 0.06 | 0.01 | 0.82 |
| 126 | 12 | 80.0 | 44.4 | 39 | 100.0 | 55.6 | — | — | Uniformly dispersed | 52.3 | 0.06 | 0.02 | 0.63 |
| 127 | 13 | 30.0 | 23.1 | 39 | 100.0 | 76.9 | — | — | Uniformly dispersed | 55.5 | 0.07 | 0.02 | 0.79 |
| 128 | 13 | 80.0 | 44.4 | 39 | 100.0 | 55.6 | — | — | Uniformly dispersed | 54.6 | 0.04 | 0.01 | 0.58 |
| 129 | 18 | 1.6 | 1.6 | 39 | 100.0 | 98.4 | — | — | Uniformly dispersed | 48.6 | 0.06 | 0.01 | 0.77 |
| 130 | 18 | 8.9 | 8.2 | 39 | 100.0 | 91.8 | — | — | Uniformly dispersed | 56.6 | 0.04 | 0.01 | 0.66 |
| 131 | 20 | 3.2 | 3.1 | 39 | 100.0 | 96.9 | — | — | Uniformly dispersed | 47.8 | 0.07 | 0.02 | 0.68 |
| 132 | 20 | 21.5 | 17.7 | 39 | 100.0 | 82.3 | — | — | Uniformly dispersed | 54.3 | 0.06 | 0.01 | 0.74 |
| 133 | 40 | 150.0 | 100.0 | — | — | — | — | — | Uniformly dispersed | 56.1 | 0.04 | 0.01 | 0.35 |
| 134 | 41 | 150.0 | 100.0 | — | — | — | — | — | Uniformly dispersed | 49.2 | 0.05 | 0.02 | 0.45 |
| 135 | 42 | 150.0 | 100.0 | — | — | — | — | — | Uniformly dispersed | 47.8 | 0.03 | 0.02 | 0.40 |
| 136 | 43 | 150.0 | 100.0 | — | — | — | — | — | Uniformly dispersed | 56.6 | 0.04 | 0.01 | 0.38 |
| 137 | 44 | 150.0 | 100.0 | — | — | — | — | — | Uniformly dispersed | 56.2 | 0.06 | 0.01 | 0.42 |
| 138 | 45 | 150.0 | 100.0 | — | — | — | — | — | Uniformly dispersed | 49.5 | 0.03 | 0.02 | 0.40 |
| 139 | 46 | 150.0 | 100.0 | — | — | — | — | — | Uniformly dispersed | 52.7 | 0.02 | 0.01 | 0.31 |

*pbw = part by weight

TABLE 30

| Membrane No. | Onium salt compound Compound No. | Weight (mg) | Compositional ratio (pbw*) | Boric diester compound Compound No. | Weight (mg) | Compositional ratio (pbw*) | Polymer Designation | Weight (mg) | State of dispersion in membrane | Slope (mV/dec) | Selectivity coefficients relative to anions NO₃⁻ | Cl⁻ | SaI⁻ |
|---|---|---|---|---|---|---|---|---|---|---|---|---|---|
| Present invention | | | | | | | | | | | | | |
| 140 | 47 | 150.0 | 100.0 | — | — | — | — | — | Uniformly dispersed | 55.4 | 0.04 | 0.01 | 0.38 |
| 141 | 48 | 150.0 | 100.0 | — | — | — | — | — | Uniformly dispersed | 54.6 | 0.04 | 0.02 | 0.45 |
| 142 | 49 | 150.0 | 100.0 | — | — | — | — | — | Uniformly dispersed | 49.9 | 0.02 | 0.01 | 0.34 |
| 143 | 50 | 150.0 | 100.0 | — | — | — | — | — | Uniformly dispersed | 55.2 | 0.02 | 0.01 | 0.41 |
| 144 | 51 | 150.0 | 100.0 | — | — | — | — | — | Uniformly dispersed | 57.3 | 0.05 | 0.02 | 0.41 |
| 145 | 52 | 150.0 | 100.0 | — | — | — | — | — | Uniformly dispersed | 49.7 | 0.03 | 0.01 | 0.30 |
| 146 | 53 | 150.0 | 100.0 | — | — | — | — | — | Uniformly dispersed | 57.0 | 0.03 | 0.01 | 0.37 |
| 147 | 54 | 150.0 | 100.0 | — | — | — | — | — | Uniformly dispersed | 54.0 | 0.05 | 0.02 | 0.37 |
| 148 | 55 | 150.0 | 100.0 | — | — | — | — | — | Uniformly dispersed | 48.8 | 0.03 | 0.01 | 0.30 |
| 149 | 56 | 150.0 | 100.0 | — | — | — | — | — | Uniformly dispersed | 50.1 | 0.03 | 0.01 | 0.42 |
| 150 | 57 | 150.0 | 100.0 | — | — | — | — | — | Uniformly dispersed | 54.6 | 0.05 | 0.02 | 0.54 |
| 151 | 58 | 150.0 | 100.0 | — | — | — | — | — | Uniformly dispersed | 54.5 | 0.04 | 0.01 | 0.32 |
| 152 | 59 | 150.0 | 100.0 | — | — | — | — | — | Uniformly dispersed | 47.9 | 0.04 | 0.01 | 0.40 |
| 153 | 60 | 150.0 | 100.0 | — | — | — | — | — | Uniformly dispersed | 56.3 | 0.05 | 0.02 | 0.40 |
| 154 | 61 | 150.0 | 100.0 | — | — | — | — | — | Uniformly dispersed | 54.8 | 0.03 | 0.01 | 0.35 |
| 155 | 62 | 150.0 | 100.0 | — | — | — | — | — | Uniformly dispersed | 57.2 | 0.03 | 0.02 | 0.40 |
| 156 | 63 | 150.0 | 100.0 | — | — | — | — | — | Uniformly dispersed | 48.2 | 0.05 | 0.02 | 0.40 |
| 157 | 64 | 150.0 | 100.0 | — | — | — | — | — | Uniformly dispersed | 56.9 | 0.03 | 0.01 | 0.33 |
| 158 | 65 | 150.0 | 100.0 | — | — | — | — | — | Uniformly dispersed | 54.6 | 0.03 | 0.01 | 0.42 |
| 159 | 66 | 150.0 | 100.0 | — | — | — | — | — | Uniformly dispersed | 54.6 | 0.05 | 0.02 | 0.42 |
| 160 | 67 | 150.0 | 100.0 | — | — | — | — | — | Uniformly dispersed | 52.9 | 0.03 | 0.01 | 0.37 |
| 161 | 68 | 150.0 | 100.0 | — | — | — | — | — | Uniformly dispersed | 54.8 | 0.04 | 0.02 | 0.48 |
| 162 | 69 | 150.0 | 100.0 | — | — | — | — | — | Uniformly dispersed | 56.7 | 0.05 | 0.02 | 0.52 |

*pbw = part by weight

TABLE 31

| Membrane No. | Onium salt compound Compound No. | Weight (mg) | Compositional ratio (pbw*) | Boric diester compound Compound No. | Weight (mg) | Compositional ratio (pbw*) | Polymer Designation | Weight (mg) | State of dispersion in membrane | Slope (mV/dec) | Selectivity coefficients relative to anions NO₃⁻ | Cl⁻ | SaI⁻ |
|---|---|---|---|---|---|---|---|---|---|---|---|---|---|
| Present invention | | | | | | | | | | | | | |
| 163 | 70 | 150.0 | 100.0 | — | — | — | — | — | Uniformly dispersed | 54.1 | 0.03 | 0.01 | 0.40 |
| 164 | 71 | 150.0 | 100.0 | — | — | — | — | — | Uniformly dispersed | 54.1 | 0.03 | 0.01 | 0.39 |
| 165 | 72 | 150.0 | 100.0 | — | — | — | — | — | Uniformly dispersed | 56.9 | 0.04 | 0.02 | 0.46 |
| 166 | 73 | 150.0 | 100.0 | — | — | — | — | — | Uniformly dispersed | 53.4 | 0.03 | 0.01 | 0.32 |
| 167 | 74 | 150.0 | 100.0 | — | — | — | — | — | Uniformly dispersed | 54.7 | 0.04 | 0.02 | 0.40 |
| 168 | 75 | 150.0 | 100.0 | — | — | — | — | — | Uniformly dispersed | 49.7 | 0.04 | 0.02 | 0.56 |
| 169 | 76 | 150.0 | 100.0 | — | — | — | — | — | Uniformly dispersed | 56.2 | 0.03 | 0.01 | 0.32 |
| 170 | 77 | 150.0 | 100.0 | — | — | — | — | — | Uniformly dispersed | 54.8 | 0.04 | 0.01 | 0.41 |
| 171 | 78 | 150.0 | 100.0 | — | — | — | — | — | Uniformly dispersed | 55.0 | 0.04 | 0.02 | 0.41 |
| 172 | 79 | 150.0 | 100.0 | — | — | — | — | — | Uniformly dispersed | 49.0 | 0.03 | 0.01 | 0.38 |
| 173 | 80 | 150.0 | 100.0 | — | — | — | — | — | Uniformly dispersed | 46.8 | 0.04 | 0.02 | 0.40 |
| 174 | 81 | 150.0 | 100.0 | — | — | — | — | — | Uniformly dispersed | 47.7 | 0.04 | 0.02 | 0.47 |
| Comparative Examples | | | | | | | | | | | | | |
| Comparative Membrane 1 | — | — | — | 23 | 100.0 | 66.7 | PVC | 50.0 | Uniformly dispersed | 10.6 | — | — | — |
| Comparative Membrane 2 | TOAB | 10.0 | 5.55 | — | — | — | PVC | 50.0 | Uniformly dispersed | 50.4 | 36.9 | 0.04 | 308.4 |
| Comparative Membrane 3 | TOTC | 5.0 | 3.16 | — | — | — | PVC | 50.0 | Uniformly dispersed | 57.9 | — | 19.95 | — |
| Comparative Membrane 4 | TOABr | 22.2 | 12.9 | — | — | — | PVC | 50.0 | Uniformly dispersed | 56.3 | 25.1 | 10.0 | — |

*pbw = part by weight

Figure 2:
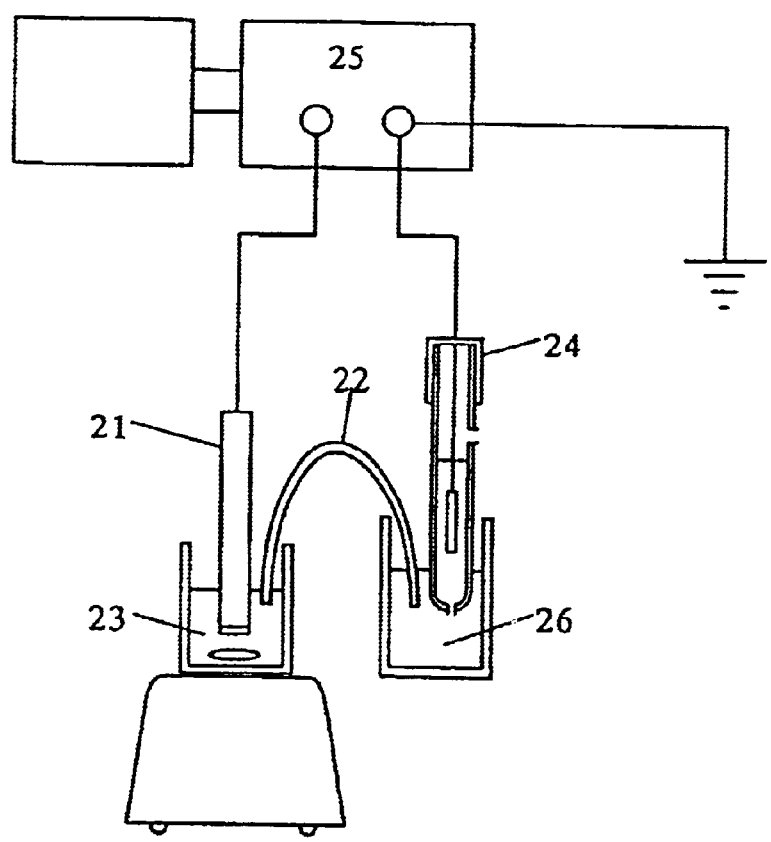
FIG. 2 is a schematic view of an apparatus for measuring an electric potential difference by using an ion-selective electrode.

Each of the membranous materials thus obtained was attached to an electrode as illustrated in FIG. 1. Then, using an apparatus as illustrated in FIG. 2, the relationship between ion concentration and electric potential difference at room temperature was measured for various anions. On the basis of the results thus obtained, the hydrogencarbonate ion selectivity coefficients relative to those anions were determined according to a well-known method [i.e., the method described in G. J. Moody and J. D. Thomas (transl. by Shin Munemori and Kazuo Hiuro), "Ion-selective Electrodes", Kyoritsu Shuppan, p. 18 (1977)]. The results thus obtained are also shown in Tables 24–31.

Comparative Example 1
(Formation of Comparative Membrane 1)

Using 50 mg of PVC (with a degree of polymerization of 1,000) and 100 mg of a boric diester compound (Compound No. 14), a membranous material was obtained in exactly the same manner as in Example 1. The state of dispersion in this membrane is also shown in Table 31. Using the membranous material thus obtained, its hydrogencarbonate ion selectivity coefficients relative to various anions were determined in the same manner as in Example 1. The results thus obtained are also shown in Tables 31. In the tables, a dash (-) indicates that no addition was made or no value was calculable.

Comparative Example 2
(Formation of Comparative Membrane 2)

Using 10 mg of tetraoctylammonium bromide (TOABr), 20 mg of 4-(n-decyl)-1-trifluoroacetylbenzene, 50 mg of PVC (with a degree of polymerization of 1,000), and 100 mg of di(2-ethylhexyl)sebacate (manufactured by Kanto Chemical Co., Inc.), a membranous material was obtained in exactly the same manner as in Example 1. The state of dispersion in this membrane is also shown in Table 31. Using the membranous material thus obtained, its hydrogencarbonate ion selectivity coefficients relative to various anions were determined in the same manner as in Example 1. The results thus obtained are also shown in Tables 31.

Comparative Example 3
(Formation of Comparative Membrane 3)

Using 5 mg of trioctyltin chloride (TOTC), 3 mg of 4-(n-decyl)-1-trifluoroacetylbenzene, 50 mg of PVC (with a degree of polymerization of 1,000), and 100 mg of di(2-ethylhexyl)sebacate, a membranous material was obtained in exactly the same manner as in Example 1. The state of dispersion in this membrane is also shown in Table 31. Using the membranous material thus obtained, its hydrogencarbonate ion selectivity coefficients relative to various anions were determined in the same manner as in Example 1. The results thus obtained are also shown in Tables 31.

Comparative Example 4
(Formation of Comparative Membrane 4)

Using 50 mg of PVC (with a degree of polymerization of 1,000), 100 mg of o-nitrophenyl octyl ether, and tetraoctadecylammonium bromide (TOAB), a membranous material was obtained in exactly the same manner as in Example 1. The state of dispersion in this membrane is also shown in Table 31. Using the membranous material thus obtained, its hydrogencarbonate ion selectivity coefficients relative to various anions were determined in the same manner as in Example 1. The results thus obtained are also shown in Tables 31.

The ion selectivity coefficients shown in the examples indicate that the hydrogencarbonate ion selectivity of the anion-sensitive membrane is better as their values become smaller. As is evident from Tables 24–31, the anion-selective electrodes using the bicarbonate ion-sensitive membrane of the present invention have excellent hydrogencarbonate ion selectivity relative to nitrate, chloride and salicylate ions present in biological fluids, and can hence measure the hydrogencarbonate ion concentrations in biological fluids accurately.

On the other hand, the membrane composed of a boric diester and PVC (Comparative Membrane 1) is not sensitive to hydrogencarbonate ion at all, and cannot measure hydrogencarbonate ion concentrations. Moreover, the membrane composed of a quaternary ammonium salt, a 4-alkyl-1-trifluoroacetylbenzene, a polymer and a plasticizer (Comparative Membrane 2), the membrane composed of trioctyltin chloride, a 4-alkyl-1-trifluoroacetylbenzene, a polymer and a plasticizer (Comparative Membrane 3), and the membrane composed of a quaternary ammonium salt, NPOE, and a polymer (Comparative Membrane 4) have insufficient hydrogencarbonate ion selectivity relative to nitrate, salicylate or chloride ion, so that it is difficut to measure the hydrogencarbonate ion concentrations in biological fluids accurately by using these membranes.

Example 2
(Formation of Membrane Nos. 175–197)

The onium salt compounds and fat-soluble anion salts shown in Table 32 were used in the respective amounts indicated in Table 32. For each Membrane No., the indicated amounts of the onium salt compound and fat-soluble anion salt, 50 mg of PVC (with a degree of polymerization of 1,000), and 100 mg of a boric diester compound (Compound No. 23) were dissolved in 2.5 ml of tetrahydrofuran, and the resulting solution was cast in a Petri dish made of glass and having a diameter of 27 mm. A membranous material was obtained by evaporating the solvent at 20° C. under atmospheric pressure for 24 hours. The state of dispersion in the membranes thus obtained is also shown in Table 32.

TABLE 32

| Membrane No. | Onium salt compound | | | Fat-soluble anion | | | State of dispersion in membrane | Slope (mV/dec) | Response speed (seconds) | Selectivity coefficients relative to anions | | |
|---|---|---|---|---|---|---|---|---|---|---|---|---|
| | Compound No. | Weight (mg) | Compositional ratio (pbw*) | Compound No. | Weight (mg) | Molar ratio | | | | $NO_3^-$ | $Cl^-$ | $Sal^-$ |
| Present invention | | | | | | | | | | | | |
| 175 | 1 | 8.1 | 5.12 | TFPB | 0.9 | 0.05 | Uniformly dispersed | 41.3 | 26 | 0.03 | 0.01 | 0.60 |
| 176 | 1 | 8.1 | 5.12 | TFPB | 1.8 | 0.10 | Uniformly dispersed | 38.9 | 20 | 0.04 | 0.01 | 0.58 |
| 177 | 1 | 8.1 | 5.12 | TFPB | 3.6 | 0.20 | Uniformly dispersed | 42.5 | 10 | 0.06 | 0.02 | 0.67 |

TABLE 32-continued

| Membrane No. | Onium salt compound | | | Fat-soluble anion | | | State of dispersion in membrane | Slope (mV/dec) | Response speed (seconds) | Selectivity coefficients relative to anions | | |
|---|---|---|---|---|---|---|---|---|---|---|---|---|
| | Compound No. | Weight (mg) | Compositional ratio (pbw*) | Compound No. | Weight (mg) | Molar ratio | | | | $NO_3^-$ | $Cl^-$ | $SaI^-$ |
| 178 | 1 | 8.1 | 5.12 | TFPB | 7.2 | 0.40 | Uniformly dispersed | 45.6 | 9 | 0.05 | 0.01 | 0.77 |
| 179 | 8 | 7.3 | 4.64 | TFPB | 0.9 | 0.05 | Uniformly dispersed | 51.3 | 42 | 0.05 | 0.01 | 0.73 |
| 180 | 8 | 7.3 | 4.64 | TFPB | 1.8 | 0.10 | Uniformly dispersed | 50.6 | 25 | 0.06 | 0.03 | 0.61 |
| 181 | 8 | 7.3 | 4.64 | TFPB | 3.6 | 0.20 | Uniformly dispersed | 48.5 | 9 | 0.04 | 0.01 | 0.58 |
| 182 | 8 | 7.3 | 4.64 | TFPB | 7.2 | 0.40 | Uniformly dispersed | 38.6 | 9 | 0.05 | 0.02 | 0.55 |
| 183 | 12 | 15.9 | 9.58 | TFPB | 0.9 | 0.05 | Uniformly dispersed | 52.0 | 21 | 0.06 | 0.01 | 0.57 |
| 184 | 12 | 15.9 | 9.58 | TFPB | 1.8 | 0.10 | Uniformly dispersed | 51.3 | 18 | 0.05 | 0.03 | 0.61 |
| 185 | 12 | 15.9 | 9.58 | TFPB | 3.6 | 0.20 | Uniformly dispersed | 43.2 | 10 | 0.05 | 0.02 | 0.63 |
| 186 | 12 | 15.9 | 9.58 | TFPB | 7.2 | 0.40 | Uniformly dispersed | 44.4 | 10 | 0.04 | 0.03 | 0.49 |
| 187 | 1 | 8.1 | 5.12 | DESS | 0.4 | 0.10 | Uniformly dispersed | 46.9 | 12 | 0.04 | 0.03 | 0.65 |
| 188 | 1 | 8.1 | 5.12 | TCPB | 3.0 | 0.30 | Uniformly dispersed | 40.5 | 15 | 0.07 | 0.02 | 0.72 |
| 189 | 8 | 7.3 | 4.64 | DESS | 0.4 | 0.10 | Uniformly dispersed | 45.3 | 17 | 0.07 | 0.03 | 0.62 |
| 190 | 8 | 7.3 | 4.64 | TCPB | 3.0 | 0.30 | Uniformly dispersed | 40.8 | 7 | 0.05 | 0.01 | 0.62 |
| 191 | 12 | 15.9 | 9.58 | DESS | 0.4 | 0.10 | Uniformly dispersed | 49.6 | 19 | 0.05 | 0.03 | 0.57 |
| 192 | 12 | 15.9 | 9.58 | TCPB | 3.0 | 0.30 | Uniformly dispersed | 43.1 | 14 | 0.06 | 0.03 | 0.51 |
| 193 | 18 | 22.8 | 13.2 | TFPB | 1.0 | 0.05 | Uniformly dispersed | 50.3 | 15 | 0.05 | 0.01 | 0.70 |
| 194 | 18 | 22.8 | 13.2 | TFPB | 3.7 | 0.20 | Uniformly dispersed | 52.1 | 7 | 0.06 | 0.02 | 0.64 |
| 195 | 18 | 22.8 | 13.2 | TFPB | 7.4 | 0.40 | Uniformly dispersed | 50.4 | 5 | 0.05 | 0.01 | 0.63 |
| 196 | 20 | 20.4 | 12.0 | TFPB | 3.2 | 0.10 | Uniformly dispersed | 54.1 | 8 | 0.04 | 0.02 | 0.43 |
| 197 | 20 | 20.4 | 12.0 | TFPB | 12.8 | 0.40 | Uniformly dispersed | 55.7 | 5 | 0.04 | 0.01 | 0.30 |

*pbw = part by weight

The onium salt compounds and fat-soluble anion salts shown in Table 33 were used in the respective amounts indicated in Table 33. For each Membrane No., the indicated amounts of the onium salt compound and fat-soluble anion salt, and 150 mg of a boric diester compound (Compound No. 39) were dissolved in 2.5 ml of tetrahydrofuran, and the resulting solution was cast in a Petri dish made of glass and having a diameter of 27 mm. A membranous material was obtained by evaporating the solvent at 20° C. under atmospheric pressure for 24 hours. The state of dispersion in the membranes thus obtained is also shown in Table 33.

TABLE 33

| Membrane No. | Onium salt compound | | | Fat-soluble anion | | | State of dispersion in membrane | Slope (mV/dec) | Response speed (seconds) | Selectivity coefficients relative to anions | | |
|---|---|---|---|---|---|---|---|---|---|---|---|---|
| | Compound No. | Weight (mg) | Compositional ratio (pbw*) | Compound No. | Weight (mg) | Molar ratio | | | | $NO_3^-$ | $Cl^-$ | $SaI^-$ |
| Present invention | | | | | | | | | | | | |
| 198 | 1 | 32.4 | 17.8 | TFPB | 3.6 | 0.05 | Uniformly dispersed | 48.3 | 15 | 0.05 | 0.01 | 0.70 |
| 199 | 1 | 32.4 | 17.8 | TFPB | 7.2 | 0.10 | Uniformly dispersed | 49.5 | 10 | 0.05 | 0.01 | 0.60 |
| 200 | 1 | 32.4 | 17.8 | TFPB | 14.4 | 0.20 | Uniformly dispersed | 57.0 | 5 | 0.04 | 0.01 | 0.52 |
| 201 | 1 | 32.4 | 17.8 | TFPB | 28.8 | 0.40 | Uniformly dispersed | 51.3 | 4 | 0.06 | 0.01 | 0.30 |
| 202 | 8 | 29.2 | 16.3 | TFPB | 3.6 | 0.05 | Uniformly dispersed | 55.5 | 21 | 0.05 | 0.01 | 0.74 |
| 203 | 8 | 29.2 | 16.3 | TFPB | 7.2 | 0.10 | Uniformly dispersed | 57.6 | 4 | 0.05 | 0.01 | 0.52 |
| 204 | 8 | 29.2 | 16.3 | TFPB | 14.4 | 0.20 | Uniformly dispersed | 52.2 | 4 | 0.05 | 0.02 | 0.33 |
| 205 | 8 | 29.2 | 16.3 | TFPB | 28.8 | 0.40 | Uniformly dispersed | 48.3 | 3 | 0.04 | 0.02 | 0.21 |
| 206 | 12 | 63.6 | 29.8 | TFPB | 3.6 | 0.05 | Uniformly dispersed | 51.7 | 18 | 0.05 | 0.02 | 0.60 |
| 207 | 12 | 63.6 | 29.8 | TFPB | 7.2 | 0.10 | Uniformly dispersed | 47.6 | 15 | 0.05 | 0.01 | 0.48 |
| 208 | 12 | 63.6 | 29.8 | TFPB | 14.4 | 0.20 | Uniformly dispersed | 50.0 | 4 | 0.04 | 0.01 | 0.34 |
| 209 | 12 | 63.6 | 29.8 | TFPB | 28.8 | 0.40 | Uniformly dispersed | 49.9 | 4 | 0.03 | 0.03 | 0.30 |
| 210 | 1 | 32.4 | 17.8 | DESS | 1.6 | 0.10 | Uniformly dispersed | 54.7 | 21 | 0.05 | 0.02 | 0.55 |
| 211 | 1 | 32.4 | 17.8 | TCPB | 12.0 | 0.30 | Uniformly dispersed | 51.3 | 5 | 0.04 | 0.01 | 0.37 |
| 212 | 8 | 29.2 | 16.3 | DESS | 1.6 | 0.10 | Uniformly dispersed | 59.0 | 15 | 0.03 | 0.03 | 0.64 |
| 213 | 8 | 29.2 | 16.3 | TCPB | 12.0 | 0.30 | Uniformly dispersed | 57.8 | 4 | 0.04 | 0.02 | 0.35 |
| 214 | 12 | 63.6 | 29.8 | DESS | 11.2 | 0.70 | Uniformly dispersed | 49.5 | 3 | 0.05 | 0.03 | 0.54 |
| 215 | 12 | 63.6 | 29.8 | TCPB | 12.0 | 0.30 | Uniformly dispersed | 47.5 | 4 | 0.04 | 0.02 | 0.31 |

TABLE 33-continued

| Membrane No. | Onium salt compound | | | Fat-soluble anion | | | State of dispersion in membrane | Slope (mV/dec) | Response speed (seconds) | Selectivity coefficients relative to anions | | |
|---|---|---|---|---|---|---|---|---|---|---|---|---|
| | Compound No. | Weight (mg) | Compositional ratio (pbw*) | Compound No. | Weight (mg) | Molar ratio | | | | $NO_3^-$ | $Cl^-$ | $SaI^-$ |
| 216 | 18 | 91.2 | 37.8 | TFPB | 4.0 | 0.05 | Uniformly dispersed | 52.2 | 10 | 0.06 | 0.02 | 0.76 |
| 217 | 18 | 91.2 | 37.8 | TFPB | 14.8 | 0.20 | Uniformly dispersed | 49.6 | 4 | 0.06 | 0.01 | 0.47 |
| 218 | 18 | 91.2 | 37.8 | TFPB | 29.6 | 0.40 | Uniformly dispersed | 52.3 | 3 | 0.04 | 0.01 | 0.29 |
| 219 | 20 | 81.6 | 35.2 | TFPB | 12.8 | 0.10 | Uniformly dispersed | 57.4 | 7 | 0.03 | 0.01 | 0.56 |
| 220 | 20 | 81.6 | 35.2 | TFPB | 51.2 | 0.40 | Uniformly dispersed | 48.5 | 3 | 0.04 | 0.01 | 0.25 |

*pbw = part by weight

Using the membranous materials thus obtained, their hydrogencarbonate ion selectivity coefficients relative to various anions were determined in the same manner as in Example 1. Moreover, their response speeds (99% response times) were measured by using a 10 mM solution of sodium hydrogencarbonate as a sample. The results thus obtained are also shown in Table 33.

In Tables 32 and 33, it is evident from Membrane Nos. 175–186 and 193–197 that, when tetrakis[3,5-bis(trifluoromethyl)phenyl]borate sodium salt, which is a fat-soluble anion salt, is added in a molar ratio of 0.1 to 0.4 based on the onium salt compound, the resulting anion-selective electrode shows an increase in response speed and can hence determine hydrogencarbonate ions rapidly. Moreover, an improvement in response speed is also noted when a fat-soluble anion salt such as di(2-ethylhexyl) sulfosuccinic acid sodium salt (DESS) or tetrakis[4-chlorophenyl]borate potassium salt (TCPB) is added (Membrane Nos. 187–192). Furthermore, an improvement in response speed is also noted when a fat-soluble anion salt is added to a membrane using a high-molecular-weight boric diester in a molar ratio of 0.1 to 0.7 based on the onium salt.

Example 3

With respect to most of the electrodes obtained in Examples 1–2 and Comparative Examples 1–4, the electric potentials of each electrode when it was immersed in a $10^{-3}$ M solution of sodium hydrogencarbonate and when it was immersed in a $10^{-2}$ M solution of sodium hydrogencarbonate were measured, and the absolute value of the difference therebetween was calculated. The results thus obtained are shown in Tables 34 and 35. After these electrodes were stored in a $10^{-1}$ M aqueous solution of sodium chloride for one year, the electric potentials of each electrode when it was immersed in $10^{-3}$ M and $10^{-2}$ M solutions of sodium hydrogencarbonate were measured in the same manner as before, and the absolute value of the difference therebetween was calculated. The results thus obtained are also shown in Tables 34 and 35. As is evident from these tables, potential changes similar to those before storage were observed even after the electrodes were stored in a $10^{-1}$ M aqueous solution of sodium chloride for one year, indicating that the electrodes have a long life.

TABLE 34

| Membrane No. | Potential difference before immersion | Potential difference after immersion |
|---|---|---|
| Present invention | | |
| 1 | 50.2 | 46.1 |
| 2 | 58.3 | 51.3 |
| 3 | 43.5 | 43.8 |
| 4 | 47.9 | 44.4 |
| 5 | 50.9 | 46.7 |
| 6 | 45.8 | 45.0 |
| 7 | 51.3 | 49.9 |
| 8 | 46.5 | 46.0 |
| 9 | 46.6 | 46.0 |
| 10 | 46.6 | 41.5 |
| 11 | 51.2 | 50.0 |
| 12 | 50.5 | 47.2 |
| 13 | 49.5 | 47.5 |
| 14 | 46.8 | 41.5 |
| 15 | 53.5 | 50.5 |
| 16 | 55.5 | 49.7 |
| 17 | 55.0 | 41.5 |
| 18 | 49.9 | 51.3 |
| 19 | 53.3 | 48.6 |
| 20 | 57.7 | 55.2 |
| 21 | 46.9 | 48.0 |
| 22 | 48.0 | 44.0 |
| 23 | 46.5 | 46.5 |
| 24 | 51.4 | 53.3 |
| 25 | 55.0 | 49.7 |
| 26 | 49.0 | 46.4 |
| 27 | 48.2 | 47.7 |
| 28 | 51.3 | 53.0 |
| 29 | 53.8 | 51.9 |
| 30 | 48.9 | 48.2 |
| 31 | 44.7 | 41.5 |
| 32 | 46.7 | 49.3 |
| 33 | 45.1 | 50.2 |
| 34 | 51.0 | 45.0 |
| 35 | 52.4 | 43.2 |
| 36 | 49.0 | 48.7 |
| 37 | 54.0 | 53.6 |
| 38 | 51.4 | 50.0 |
| 39 | 51.6 | 49.9 |
| 40 | 45.3 | 49.8 |
| 41 | 43.9 | 46.5 |
| 42 | 51.6 | 52.7 |
| 43 | 54.7 | 49.1 |
| 44 | 46.2 | 49.8 |
| 45 | 49.8 | 49.0 |
| 46 | 56.3 | 51.3 |
| 47 | 51.2 | 53.2 |
| 48 | 52.2 | 52.2 |
| 49 | 48.3 | 49.0 |
| 50 | 46.9 | 43.5 |
| 51 | 53.6 | 49.9 |

TABLE 34-continued

| Membrane No. | Potential difference before immersion | Potential difference after immersion |
| --- | --- | --- |
| 52 | 51.7 | 50.4 |
| 53 | 47.4 | 47.0 |
| 54 | 45.8 | 44.4 |
| 55 | 44.4 | 41.3 |
| 56 | 47.4 | 44.0 |
| 57 | 46.5 | 50.1 |
| 58 | 57.1 | 53.3 |
| 59 | 53.7 | 53.9 |
| 60 | 56.6 | 52.1 |
| 61 | 41.3 | 48.6 |
| 62 | 38.9 | 45.4 |
| 63 | 42.5 | 48.3 |
| 64 | 45.6 | 38.8 |
| 65 | 51.3 | 49.2 |
| 66 | 50.6 | 49.2 |
| 67 | 48.5 | 46.6 |
| 68 | 38.6 | 43.0 |
| 69 | 52.0 | 54.4 |
| 70 | 51.3 | 50.7 |

TABLE 35

| Membrane No. | Potential difference before immersion | Potential difference after immersion |
| --- | --- | --- |
| Present invention | | |
| 71 | 43.2 | 48.2 |
| 72 | 44.4 | 48.0 |
| 73 | 46.9 | 52.3 |
| 74 | 40.5 | 53.6 |
| 75 | 45.3 | 50.0 |
| 76 | 40.8 | 43.2 |
| 77 | 49.6 | 45.3 |
| 78 | 43.1 | 38.1 |
| 79 | 46.5 | 50.2 |
| 80 | 54.4 | 55.3 |
| 84 | 48.8 | 40.5 |
| 88 | 56.3 | 53.8 |
| 92 | 47.6 | 45.5 |
| 94 | 54.1 | 56.0 |
| 98 | 52.0 | 56.3 |
| 100 | 48.9 | 50.5 |
| 105 | 56.9 | 54.3 |
| 110 | 52.1 | 55.7 |
| 115 | 45.9 | 54.8 |
| 120 | 56.0 | 56.1 |
| 125 | 49.7 | 45.3 |
| 130 | 56.6 | 54.8 |
| 135 | 47.8 | 51.3 |
| 140 | 55.4 | 58.0 |
| 145 | 49.7 | 53.1 |
| 150 | 54.6 | 57.6 |
| 155 | 57.2 | 53.7 |
| 160 | 52.9 | 57.4 |
| 165 | 56.9 | 51.3 |
| 170 | 54.8 | 49.9 |
| 180 | 50.6 | 51.3 |
| 190 | 40.8 | 48.5 |
| 200 | 57.0 | 54.9 |
| 205 | 48.3 | 51.2 |
| 210 | 54.7 | 48.0 |
| 220 | 48.5 | 50.9 |
| Comparative Examples | | |
| Comparative Membrane 1 | 10.6 | 5.0 |
| Comparative Membrane 2 | 50.4 | 49.9 |
| Comparative | 57.9 | 55.5 |

TABLE 35-continued

| Membrane No. | Potential difference before immersion | Potential difference after immersion |
| --- | --- | --- |
| Membrane 3 Comparative Membrane 4 | 56.3 | 51.7 |

What is claimed is:

1. A membrane sensitive to bicarbonate ion comprising a polymer membrane which contains an onium salt structural unit (A) and an aromatic boric diester structural unit (B) of the formula

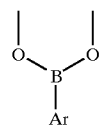

wherein Ar is an aromatic carbocyclic group which may optionally have one or more substituents, either in the form of low-molecular-weight compounds dispersed in the polymer or in a form introduced into a polymer molecule.

2. The membrane sensitive to bicarbonate ion as claimed in claim 1 wherein the polymer membrane contains the onium salt structural unit (A) in the form of an onium salt compound selected from the group consisting of a quaternary ammonium salt, a pyridinium salt, a phosphonium salt, a sulfonium salt, an oxinium salt and an arsonium salt.

3. The membrane sensitive to bicarbonate ion as claimed in claim 2 wherein the onium salt compound is an onium salt compound selected from the group consisting of compounds of the following formulae (1), (13), (14) and (15):

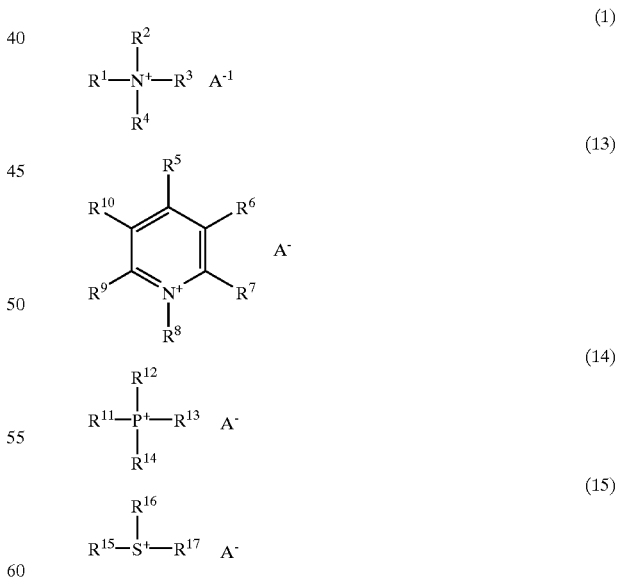

in which $R^1$ to $R^{17}$ are each independently a hydrogen atom or an organic group, and $A^-$ is an anion.

4. The membrane sensitive to bicarbonate ion as claimed in claim 3 wherein the organic group is represented by the following formula (2a), (2b) or (2c):

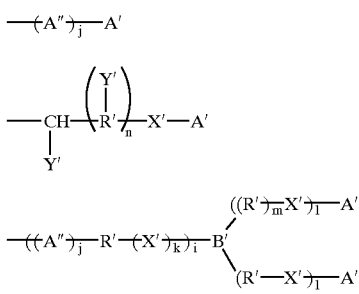
(2a)
(2b)
(2c)

in which A' is a monovalent aliphatic hydrocarbon radical that may have an ether linkage, or a monovalent aromatic hydrocarbon radical that may have an ether linkage; A" is a divalent aliphatic hydrocarbon radical that may have an ether linkage, or a divalent aromatic hydrocarbon radical that may have an ether linkage, Y' is a hydrogen atom or —R'—X'—A', B' is —N<, —CH< or

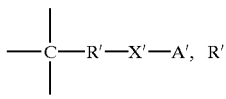

is a divalent or trivalent aliphatic hydrocarbon radical or aromatic hydrocarbon radical, X' is —O—, —CO—, —COO— or —CONH—; i, j, k, l, m and n are each 0 or 1; when a plurality of R' radicals are present in one organic group, the plurality of R' radicals may be the same or different; and the same shall apply to X' and A'.

5. The membrane sensitive to bicarbonate ion as claimed in claim 3 wherein the onium salt compound is a quaternary ammonium salt of formula (1).

6. The membrane sensitive to bicarbonate ion as claimed in claim 5 wherein the quaternary ammonium salt is a quaternary ammonium salt selected from the group consisting of compounds of the following formulae (11a) and (11b):

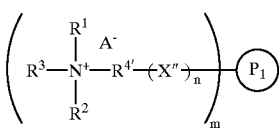
(11a)

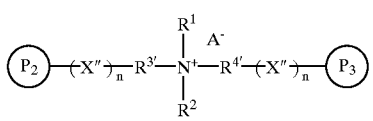
(11b)

in which $R^1$ to $R^3$ are each independently a hydrogen atom or an organic group, $A^-$ is an anion, $R^{3'}$ and $R^{4'}$ are each independently a divalent organic group, X" is a linking group such as

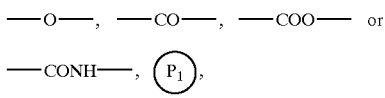

is an m valent residue obtained by removing m groups or atoms from a polymer backbone,

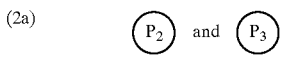

are each independently a monovalent moiety obtained by removing one group or atom from a polymer backbone, m is an integer of 1 or greater, and n is 0 or 1.

7. The membrane sensitive to bicarbonate ion as claimed in claim 1 wherein the polymer membrane contains the aromatic boric diester structural unit (B) derived from an aromatic boric diester compound of the following formula (16):

(16)

in which $X^1$ and $X^2$ are each independently an organic group, or $X^1$ and $X^2$ are combined with the atoms adjacent thereto so as to form a ring structure, Ar' is an aromatic hydrocarbon radical, Z is a hydrogen atom or an organic group, and s is an integer of 1 or greater.

8. The membrane sensitive to bicarbonate ion as claimed in claim 7 wherein the aromatic boric diester compound is a compound of the following formula (17):

(17)

in which X is a polymerizable unsaturated group-containing divalent organic group having two or more carbon atoms.

9. The membrane sensitive to bicarbonate ion as claimed in claim 7 wherein the combined $X^1$ and $X^2$ are represented by the following formula (19a) or (19b):

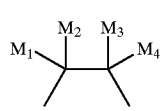
(19a)

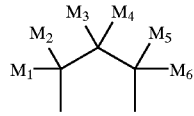
(19b)

in which $M_1$ to $M_6$ are each independently a hydrogen atom or an organic group.

10. The membrane sensitive to bicarbonate ion as claimed in claim 1 wherein the aromatic boric diester is a polymer consisting of repeating units of the structural unit (B) is represented by following formula (18):

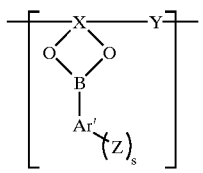
(18)

in which Y is a group derived from a compound having a group copolymerizable with a polymerizable unsaturated group, X is a tetravalent organic group having two or more carbon atoms, Ar' is an aromatic hydrocarbon radical, Z is a hydrogen atom or an organic group, and s is an integer of 1 or greater.

11. The membrane sensitive to bicarbonate ion as claimed in claim 7 wherein the aromatic boric diester compound is selected from the group consisting of compounds of the following formulae (22a) and (22b):

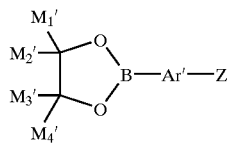
(22a)

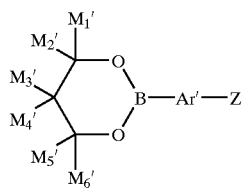
(22b)

in which $M_1'$ to $M_6'$ are independently a hydrogen atom, a methyl group, or a group derived from a polymer, Ar' is an aromatic hydrocarbon radical, Z is an aliphatic hydrocarbon radical of 1 to 72 carbon atoms or a group comprising two aliphatic hydrocarbon radicals joined to each other by means of —O—, —CO— or —COO—.

12. The membrane sensitive to bicarbonate ion as claimed in claim 1 wherein the onium salt structural unit (A) and the aromatic boric diester structural unit (B) are contained in the form of an aromatic boric diester compound selected from the group consisting of compounds of the following formulae (23), (24) and (25):

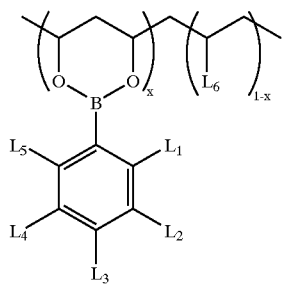
(23)

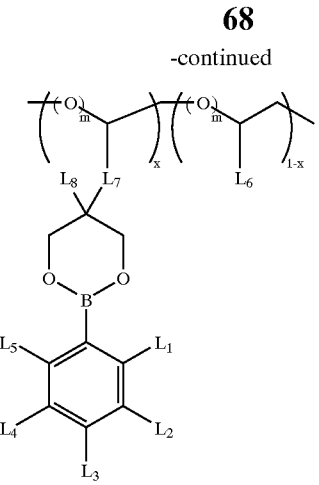
(24)

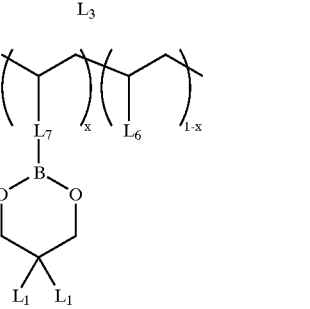
(25)

in which at least one of $L_1$ to $L_5$ is a branched or straight-chain alkyl group of 1 to 72 carbon atoms that may have —O—, —CO—, —COO—, —CONH—, —CON< or —N=CH—, and the others are hydrogen atoms; $L_6$ is a group containing a quaternary ammonium salt group; $L_7$ is a divalent organic group of 1 to 8 carbon atoms; $L_8$ is a hydrogen atom or an alkyl group of 1 to 3 carbon atoms; m is 0 or 1; and 0<x<1.

13. The membrane sensitive to bicarbonate ion as claimed in claim 1 wherein the polymer membrane contains the onium salt structural unit (A) and the aromatic boric diester structural unit (B) in such proportions that the molar ratio of (B) to (A) is in the range of 0.1 to 100,000.

14. The membrane sensitive to bicarbonate ion as claimed in claim 1 wherein the polymer membrane contains a polymer matrix having a membrane-forming ability.

15. The membrane sensitive to bicarbonate ion as claimed in claim 1 wherein the polymer membrane further contains a fat-soluble anion salt.

16. The membrane sensitive to bicarbonate ion as claimed in claim 15 wherein the ratio of the number of moles of the fat-soluble anion salt to the number of moles of the onium salt compound is in the range of 0.1 to 0.7.

17. The composition sensitive to bicarbonate ion comprising an onium salt compound and an aromatic boric diester compound.

18. The composition as claimed in claim 17 wherein the onium salt compound is an onium salt compound selected from the group consisting of compounds of the following formulae (1), (13), (14) and (15):

$$R^1 \underset{\underset{R^4}{|}}{\overset{\overset{R^2}{|}}{N^+}} R^3 \quad A^-$$
(1)

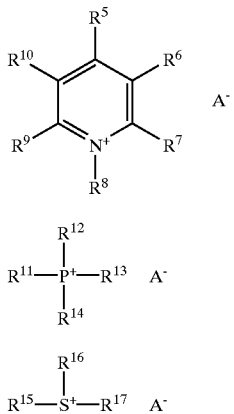

(13)

(14)

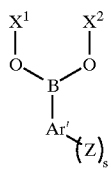

(15)

in which $R^1$ to $R^{17}$ are each independently a hydrogen atom or an organic group, and $A^-$ is an anion.

19. The composition as claimed in claim 18 wherein the aromatic boric diester compound is an aromatic boric diester compound of the following formula (16):

(16)

in which $X^1$ and $X^2$ are each independently an organic group, or $X^1$ and $X^2$ are combined with the atoms adjacent thereto so as to form a ring structure, Ar' is an aromatic hydrocarbon radical, Z is a hydrogen atom or an organic group, and s is an integer of 1 or greater.

20. The bicarbonate ion-selective electrode constructed by using a membrane sensitive to bicarbonate ion as claimed in claim 1.

21. The bicarbonate ion-selective electrode comprising a membrane sensitive to bicarbonate ion as claimed in claim 1, an internal reference electrode, and an internal electrolyte or ionic conductive substance interposed therebetween.

22. An aromatic boric diester compound represented by the following formula (23), (24) or (25):

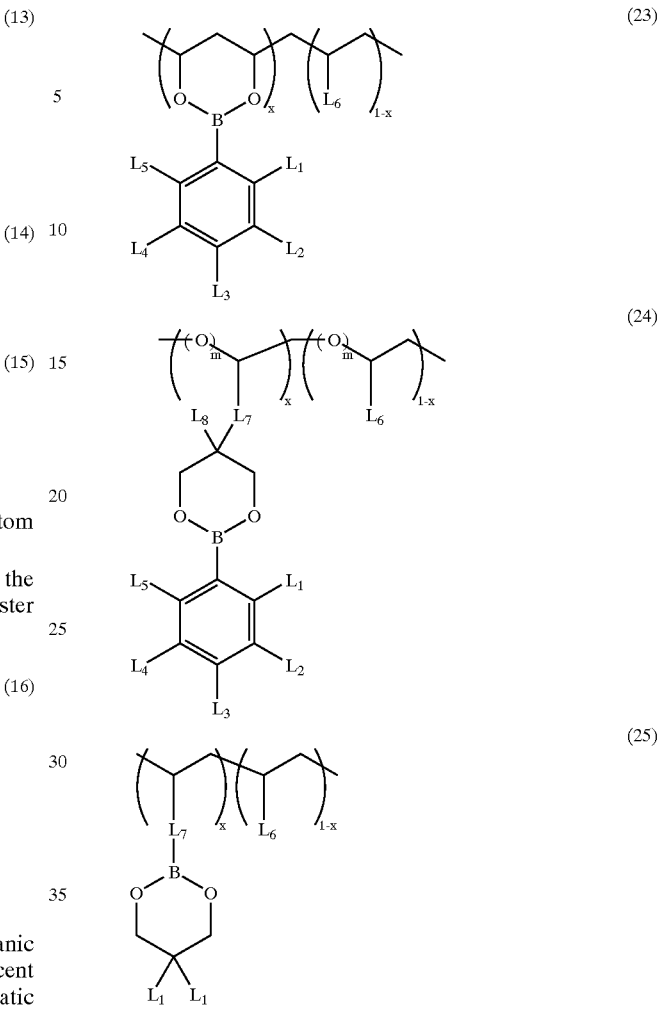

which at least one of $L_1$ to $L_5$ is a branched or straight-chain alkyl group of 1 to 72 carbon atoms that may have —O—, —CO—, —COO—, —CONH—, —CON< or —N=CH—, and the others are hydrogen atoms; $L_6$ is a group containing a quarternary ammonium salt group; $L_7$ is a divalent organic group of 1 to 8 carbon atoms; $L_8$ is a hydrogen atom or an alkyl group of 1 to 3 carbon atoms; m is 0 or 1; and $0<x<1$.

* * * * *